United States Patent
Fukunaga et al.

(10) Patent No.: US 10,244,691 B2
(45) Date of Patent: Apr. 2, 2019

(54) ROOT-KNOT NEMATODE RESISTANCE MARKER FOR TOMATO PLANT, ROOT-KNOT NEMATODE RESISTANT TOMATO PLANT, PRODUCTION METHOD FOR ROOT-KNOT NEMATODE RESISTANT TOMATO PLANT, AND SCREENING METHOD FOR ROOT-KNOT NEMATODE RESISTANT TOMATO PLANT

(71) Applicant: TAKII & COMPANY LIMITED, Kyoto-shi, Kyoto (JP)

(72) Inventors: Yutaka Fukunaga, Kyoto (JP); Takehiro Yokokawa, Kyoto (JP); Kazuo Kosugi, Kyoto (JP); Ryohei Arimoto, Kyoto (JP); Makoto Endo, Kyoto (JP); Hitomi Aoike, Kyoto (JP)

(73) Assignee: Takii & Company Limited, Kyoto (JP)

( * ) Notice: Subject to any disclaimer, the term of this patent is extended or adjusted under 35 U.S.C. 154(b) by 153 days.

(21) Appl. No.: 14/902,775

(22) PCT Filed: Jul. 4, 2014

(86) PCT No.: PCT/JP2014/067982
§ 371 (c)(1),
(2) Date: Jan. 4, 2016

(87) PCT Pub. No.: WO2015/002318
PCT Pub. Date: Jan. 8, 2015

(65) Prior Publication Data
US 2016/0165824 A1 Jun. 16, 2016

(30) Foreign Application Priority Data
Jul. 5, 2013 (JP) .................................. 2013-141865

(51) Int. Cl.
*A01H 5/10* (2018.01)
*A01H 1/02* (2006.01)
*A01H 1/04* (2006.01)
*C12Q 1/6895* (2018.01)
*A01H 5/08* (2018.01)

(52) U.S. Cl.
CPC .................. *A01H 1/02* (2013.01); *A01H 1/04* (2013.01); *A01H 5/08* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 6,613,962 B1 | 9/2003 | Vas et al. |
| 2004/0006787 A1 | 1/2004 | Martin et al. |
| 2005/0278804 A1 | 12/2005 | Hoogstraten et al. |

FOREIGN PATENT DOCUMENTS

| JP | 2001-500006 A | 1/2001 |
| JP | 2005-237380 A | 9/2005 |
| WO | 01/18191 A2 | 3/2001 |
| WO | 2008/091153 A1 | 7/2008 |
| WO | 2008/091154 A1 | 7/2008 |

OTHER PUBLICATIONS

Groenewegen et al., 1994, HortScience 29: 1088.*
Solanum pennellii chromosome ch04, NCBI/GenBank accession No. HG975443, published Nov. 19, 2015.*
Predicted Solanum pennellii putative pentatricopeptide repeat-containing protein At5g08310, mitochondrial (LOC107016104), NCBI/GenBank accession No. XM_015216588, published Dec. 23, 2015.*
Eshed and Zamir, 1995, Genetics 141: 1147-1162.*
Frary et al., 2004, Theor. Appl. Genet. 108: 485-496.*
Extended European Search Report issued in corresponding European Patent Application No. 14819579.5 dated Mar. 17, 2017.
Sim et al., "Development of a Large SNP Genotyping Array and Generation of High-Density Genetic Maps in Tomato," PLOS One, 7: e40563 (2012).
Williamson et al., "Nematode Pathogenesis and Resistance in Plants," The Plant Cell, 8: 1735-1745 (1996).
International Search Report issued in corresponding International Patent Application No. PCT/JP2014/067982 dated Oct. 7, 2014.
Bleve-Zacheo et al., "The Contribution of Biotechnology to Root-Knot Nematode Control in Tomato Plants," Pest Technology, 1: 1-16 (2007).
Wang et al., "Mapping of Heat-Stable Gene for Resistance to Southern Root-Knot Nematode in Solanum lycopersicum," Plant Molecular Biology Reporter, 31: 352-362 (2013).
Yaghoobi et al., "Mapping a new nematode resistance locus in Lycopersicon peruvianum," Theoretical and Applied Genetics, 91: 457-464 (1995).
Cap et al., "Inheritance of heat-stable resistance to Meloidogyne incognita in Lycopersicon peruvianum and its relationship to the Mi gene," Theoretical and Applied Genetics, 85: 777-783 (1993).
Veremis et al., "Mapping a novel heat-stable resistance to Meloidogyne in Lycopersicon peruvianum," Theoretical and Applied Genetics, 98: 274-280 (1999).
Hamilton et al., "Single Nucleotide Polymorphism Discovery in Cultivated Tomato via Sequencing by Synthesis," The Plant Genome, 5: 17-29 (2012).

(Continued)

*Primary Examiner* — Bratislav Stankovic
(74) *Attorney, Agent, or Firm* — Morgan, Lewis & Bockius LLP

(57) ABSTRACT

The present invention provides: a root-knot nematode resistance marker for tomato plants; a novel root-knot nematode resistant tomato plant; a method for producing a root-knot nematode resistant tomato plant; and a screening method for a root-knot nematode resistant tomato plant.

21 Claims, 1 Drawing Sheet
Specification includes a Sequence Listing.

(56) References Cited

OTHER PUBLICATIONS

Blanca et al., Variation Revealed by SNP Genotyping and Morphology Provides Insight into the Origin of the Tomato, PLOS ONE, 7: e48198 (2012).

Vos et al., "The tomato Mi-1 gene confers resistance to both root-knot nematodes and potato aphids," Nature Biotechnology, 16: 1365-1369 (1998).

Yaghoobi et al., "Fine mapping of the nematode resistance gene Mi-3 in Solanum peruvianum and construction of a S. lycopersicum DNA contig spanning the locus," Molecular Genetics & Genomics, 274: 60-69 (2005).

Jablonska et al., "The Mi-9 Gene from Solanum arcanum Conferring Heat-Stable Resistance to Root-Knot Nematodes is a Homolog of Mi-1," Plant Physiology, 143: 1044-1054 (2007).

Arens et al., "Development and evaluation of robust molecular markers linked to disease resistance in tomato for distinctness, uniformity and stability testing," Theoretical and Applied Genetics, 120: 655-664 (2010).

* cited by examiner

Root gall severity: 4  Root gall severity: 0
(B-barrier)           (deposited line)

ROOT-KNOT NEMATODE RESISTANCE MARKER FOR TOMATO PLANT, ROOT-KNOT NEMATODE RESISTANT TOMATO PLANT, PRODUCTION METHOD FOR ROOT-KNOT NEMATODE RESISTANT TOMATO PLANT, AND SCREENING METHOD FOR ROOT-KNOT NEMATODE RESISTANT TOMATO PLANT

A computer readable text file, entitled "SequenceListing.txt," created on or about Dec. 22, 2015 with a file size of about 8 kb contains the sequence listing for this application and is hereby incorporated by reference in its entirety.

TECHNICAL FIELD

The present invention relates to a root-knot nematode resistance marker for tomato plants, a root-knot nematode resistant tomato plant, a method for producing a root-knot nematode resistant tomato plant, and a screening method for a root-knot nematode resistant tomato plant.

BACKGROUND ART

In cultivation of tomato plants, insect damage by root-knot nematodes is a serious problem worldwide. Plant bodies infected with the root-knot nematodes grow poorly or may wither, for example. Thus, root-knot nematode damage leads to the reduction in the total yield of tomato plants, and the amount of damage is estimated to reach at least 100 billion yen (Non-Patent Document 1). Accordingly, with the aim of preventing the infection with root-knot nematodes, heat treatment of soil, sterilization of soil using a root knot nematocide, etc. are performed to exterminate the root-knot nematodes. These methods, however, require a large amount of labor and cost.

In recent years, in order to address such problems, attempts have been made to breed tomato cultivars resistant to various root-knot nematodes utilizing root knot nematode resistance genes. Specifically, it has been reported that tomato cultivars resistance to the southern root-knot nematode (*Meloidogyne incognita*), the peanut root-knot nematode (*Meloidogyne arenaria*), the javanese root-knot nematode (*Meloidogyne javanica*), and the like were bred utilizing a resistance gene Mi-1 derived from *Solanum peruvianum*. However, it has been revealed that the tomato cultivars having the resistance gene Mi-1 have a problem in that the resistance gene Mi-1 does not function in an environment at a soil temperature of 28° C. or higher (Non-Patent Document 2).

On this account, further research has been made on resistance genes that function without depending on temperature conditions. Root-knot nematode resistant wild tomato species *S. peruvianum* PI270435, PI1126443, LA1708, and LA2157 have resistance genes that do not depend on temperature conditions, and Mi-2, Mi-3, Mi-4, Mi-5, Mi-6, Mi-7, Mi-8, Mi-9, etc. have been reported as resistance genes derived therefrom. Also, it has been reported that, among these resistance genes, Mi-3 is located on chromosome 12 and Mi-9 is located on chromosome 6 (Non-Patent Documents 1, 3, 4, and 5). However, *S. peruvianum* plants having these resistance genes show low cross-compatibility with *Solanum lycoperiscum* plants cultivated generally as edible tomatoes. This makes the seed production of *S. lycopersicum* plants having the above resistance genes very difficult.

Under these circumstances, only the resistance gene Mi-1 obtained by selecting root-knot nematode resistant individuals after crossing and embryo culture is used in commercially available varieties of tomato plants at present, although the root-knot nematode resistance conferred by the resistance gene Mi-1 has a problem of the above-described temperature dependence.

CITATION LIST

Non-Patent Document(s)

Non-Patent Document 1: Teresa Bleve-Zacheo et al., The Contribution of Biotechnology to Root-Knot Nematode Control in Tomato Plants Pest Technology (2007), volume 1, issue 1, pp. 1-16

Non-Patent Document 2: Yinlei Wang et al., Mapping of a Heat-Stable Gene for Resistance to Southern Root-Knot Nematode in *Solanum lycopersicum* Plant Molecular Biology Reporter, April 2013, Volume 31, Issue 2, pp. 352-362

Non-Patent Document 3: J. Yaghoobi et al., Mapping a new nematode resistance locus in *Lycopersicon peruvianum* Theoretical and applied genetics (1995) 91, pp. 457-464

Non-Patent Document 4: G. B. Cap et al., Inheritance of heat-stable resistance to *Meloidogyne incognita* in *Lycopersicon peruvianum* and its relationship to the Mi gene Theoretical and applied genetics (1993) 85, pp. 777-783

Non-Patent Document 5: J. C. Veremis et al., Mapping a novel heat-stable resistance to *Meloidogyne* in *Lycopersicon peruvianum* Theoretical and applied genetics (1999) 98, pp. 274-280

BRIEF SUMMARY OF THE INVENTION

Problem to be Solved by the Invention

With the going in mind, it is an object of the present invention to provide: a root-knot nematode resistance marker for tomato plants, exhibiting dominantly inherited root-knot nematode resistance; a novel root-knot nematode resistant tomato plant that includes a dominant root-knot nematode resistance locus and exhibits root-knot nematode resistance without depending on temperature conditions in a growing environment; a method for producing a root-knot nematode resistant tomato plant using the same; and a screening method for a root-knot nematode resistant tomato plant.

Means for Solving Problem

In order to achieve the above object, the present invention provides a root-knot nematode resistance marker for a tomato plant, including a root-knot nematode resistance locus on chromosome 4.

The present invention also provides a root-knot nematode resistant tomato plant including a root-knot nematode resistance locus on chromosome 4.

The present invention also provides a method for producing a root-knot nematode resistant tomato plant, including the following steps (a) and (b):
(a) crossing the root-knot nematode resistant tomato plant according to the present invention with another tomato plant; and
(b) selecting a root-knot nematode resistant tomato plant from one or more tomato plants obtained in the step (a) or progeny lines thereof.

The present invention also provides a screening method for a root-knot nematode resistant tomato plant, including the step of as a parent for producing a root-knot nematode resistant tomato plant by crossing, selecting a tomato plant including, as a root-knot nematode resistance marker for a tomato plant, a root-knot nematode resistance locus on chromosome 4 from tomato plants to be examined.

Effects of the Invention

The inventors of the present invention conducted diligent studies, and discovered a root-knot nematode resistance locus on chromosome 4 as a root-knot nematode resistance marker for tomato plants (also referred to simply as "resistance marker" hereinafter) exhibiting dominantly inherited root-knot nematode resistance. A tomato plant including the above-described resistance marker exhibits dominantly inherited root-knot nematode resistance. Thus, the root-knot nematode resistance marker for tomato plants according to the present invention enables easy screening of a root-knot nematode resistant tomato plant, for example. Also, the root-knot nematode resistant tomato plant according to the present invention includes, for example, the root-knot nematode resistance locus on chromosome 4, so that it can exhibit root-knot nematode resistance without depending on temperature conditions in a growing environment, for example. Also, because the root-knot nematode resistant tomato plant according to the present invention includes, for example, a dominant resistance gene locus, it is possible to obtain progenies exhibiting root-knot nematode resistance inherited dominantly by crossing with other tomato plants. Furthermore, because the present invention can eliminate the necessity of soil treatments performed conventionally, the problem of labor and cost by the soil treatments also can be avoided, for example.

MODE FOR CARRYING OUT THE INVENTION

Figure 1:
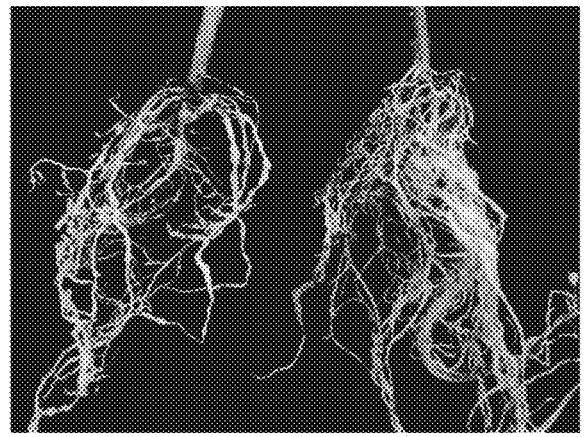
FIG. 1 is a photograph showing the evaluation criteria for root gall severity in tomato plants in Example 1.

1. Root-knot Nematode Resistance Marker for Tomato Plants

As described above, the root-knot nematode resistance marker for tomato plants according to the present invention includes a root-knot nematode resistance locus on chromosome 4. The root-knot nematode resistance marker according to the present invention is characterized in that it includes a root-knot nematode resistance locus on chromosome 4, and other configurations and conditions are not particularly limited.

In the present invention, "tomato plants" are plants classified in Section *Lycopersicon* in the subgenus *Solmum sensu stricto* of the genus *Solanum*. Specific examples thereof include *S. lycopersicum, S. peruvianum, S. arcanum Peralta, S. chilense, S. comeliomulleri, S. huaylasense Peralta, S. cheesmaniae* (L. Riley) Fosberg, *S. chmielewskii, S. galapagense* S. C. Darwin & Peralta, *S. habrochaites, S. neorickii, Solanum pennellii,* and *S. pimpinellifolium*. Among them, *S. lycopersicum* is preferable because it can be crossed easily.

In the present invention, the root-knot nematode may be, for example, southern root-knot nematode, peanut root-knot nematode, javanese root-knot nematode, *Meloidogyne microcephala*, or the like.

The term "root-knot nematode resistance" as used herein also may be referred to as "root-knot nematode tolerance", for example. The resistance means the ability to inhibit or suppress the occurrence and progression of damage due to the infection with root-knot nematodes, for example. Specifically, the resistance may mean any of the following, for example: to prevent the damage from occurring; to stop the progression of the damage that has occurred already, and to suppress (or to inhibit) the progression of the damage that has occurred already.

The root-knot nematode resistance marker according to the present invention includes the root-knot nematode resistance locus on chromosome 4. It is to be noted, however, that a tomato plant having the root-knot nematode resistance locus may have the root-knot nematode resistance locus on, instead of chromosome 4, any chromosome other than chromosome 4, for example. That is, the tomato plant including a root-knot nematode resistance locus may have the above-described root-knot nematode resistance locus on chromosome 4 on any of chromosome 1, chromosome 2, chromosome 3, chromosome 5, chromosome 6, chromosome 7, chromosome 8, chromosome 9, chromosome 10, chromosome 11, and chromosome 12.

The root-knot nematode resistant gene locus refers to a quantitative trait locus or a gene region that confers the root-knot nematode resistance. In general, QTL (quantitative trait loci) refers to a chromosome region that is involved in the expression of a quantitative trait. The QTL can be specified using a molecular marker that indicates a specific locus on a chromosome. The technique for specifying the QTL using the molecular marker is well known in the art.

In the present invention, a molecular marker used for specifying the root-knot nematode resistance locus is not particularly limited. Examples of the molecular marker include SNP markers, AFLP (amplified fragment length polymorphism) markers, RFLP (restriction fragment length polymorphism) markers, microsatellite markers, SCAR (sequence-characterized amplified region) markers, and CAPS (cleaved amplified polymorphic sequence) markers.

In the present invention, one SNP marker may be used, or two or more SNP markers may be used in combination, for example.

In the present invention, the root-knot nematode resistance locus may be specified (also referred to as "identified" hereinafter) by, for example: (1) the SNP marker; (2) a base sequence including the SNP marker; (3) a base sequence in a region between sites of two SNP markers; or any combination thereof. When the root-knot nematode resistance locus is specified by any combination of (1) to (3), the combination is not particularly limited, and examples thereof include the following combinations:
the combination of (1) and (2);
the combination of (1) and (3);
the combination of (2) and (3); and
the combination of (1), (2), and (3).

(1) Identification by SNP Marker

The root-knot nematode resistance locus may be specified by the SNP marker, as described in the item (1) above, for example. The SNP marker is not particularly limited, and examples thereof include solcap_snp_sl_21346, solcap_snp_sl_21364, TK43, YU06, YK66, TY38, AR02, HT12, solcap_snp_sl_64250, solcap_snp_sl_21383, solcap_snp_sl_21385, and solcap_snp_sl_21390. Indication of SNP markers as "solcap_snp_sl_[specific number]" is apparent to those skilled in the art in view of the common general technical knowledge as of the filing date of the present application. Information on the SNP markers is available on the web site of the SOL Genomics Network (solgenomics.net/). TK43, YU06, YK66, TY38, AR02, and HT12 are SNP markers newly identified by the inventors of the present invention, and those skilled in the art can identify the chromosomal locations of these SNP markers on the basis of the base sequences including the SNP markers to be described below. As to the analysis of these SNPs, the following literatures can be referred to, for example. Literature: Hamilton JP, Sim SC, Stoffel K, Van Deynze A, Buell CR, et al. (2012) Single Nucleotide Polymorphism Discovery in Cultivated Tomato via Sequencing by Synthesis. The Plant Genome 5. Literature: Sim S-C, Durstewitz G, Plieske J, Wieseke R, Ganal MW, et al. (2012) Development of a Large SNP Genotyping Array and Generation of High-Density. Genetic Maps in Tomato. PLoS ONE 7(7) Literature: Blanca J, Cañnizares J, Cordero L, Pascual L, Diez MJ, et al. (2012) Variation Revealed by SNP Genotyping and Morphology Provides Insight into the Origin of the Tomato. PLoS ONE 7 (10)

The solcap_snp_sl_21346 (also referred to as "SNP (a)" hereinafter) is a polymorphism such that the underlined base in brackets in SEQ ID NO: 15 is G, for example. That is, for example, a tomato plant is resistant to root-knot nematodes when the underlined base is G, and is susceptible to root-knot nematodes when the underlined base is other than G (e.g., A). The base sequence of SEQ ID NO: 15 can be obtained from the tomato plant deposited under Accession No. FERM BP-22251 to be described below, for example.

SEQ ID NO: 15
5'-CCAGAATTTATCGTGGTGGA[G]GTTCTTGGAACTGCATGGAG-3'

The SNP (a) can be identified on the basis of known information in the database of the above-described web site etc., for example. The base sequence of SEQ ID NO: 1 is identical to the base sequence of Heinz (Cultivar Name: Heinz 1706) except for the SNP (a), for example, and the underlined base in brackets is a polymorphism corresponding to the SNP (a). That is, for example, a tomato plant is resistant to root-knot nematodes when the underlined base is G, and is susceptible to root-knot nematodes when the underlined base is other than G (e.g., A). Thus, the location of the SNP (a) can be identified on the basis of information on the known base sequence of Heinz, for example.

SEQ ID NO: 1
5'-ATGCTTTCTTCAACTCCGACTTCTGTAATACCAGAATTTATCGTGGT

GGA[G]GTTCCGGGAACTGCATGGAGGAAGGTTTTAACCCCAGTTCAATC

CATATA-3'

The solcap_snp_sl_21364 (also referred to as "SNP (b)" hereinafter) is a polymorphism such that the underlined base in brackets in SEQ ID NO: 17 is T, for example. That is, for example, a tomato plant is resistant to root-knot nematodes when the underlined base is T, and is susceptible to root-knot nematodes when the underlined base is other than T (e.g., C). The base sequence of SEQ ID NO: 17 can be obtained from the tomato plant deposited under Accession No. FERM BP-22251 to be described below, for example.

SEQ ID NO: 17
5'-GTTAGTAGCAATTCA[T]GATGATCGATGGATC-3'

The SNP (b) can be identified on the basis of known information in the database of the above-described web site etc., for example. The base sequence of SEQ ID NO: 8 is identical to the base sequence of Heinz except for the SNP (b), for example, and the underlined base in brackets is a polymorphism corresponding to the SNP (b). That is, for example, a tomato plant is resistant to root-knot nematodes when the underlined base is T, and is susceptible to root-knot nematodes when the underlined base is other than T (e.g., C). Thus, the location of the SNP (b) can be identified on the basis of information on the known base sequence of Heinz, for example.

SEQ ID NO: 8
5'-TGGTGAAGAAGCTTGATCGAGTTGGTGCCCGCCTTGTTAGTAGCAAT

TCA[T]GATGATCGATGGATCAATCAATCAATCAACTATGCCTCAATTCC

AAACGA-3'

The TK43 (also referred to as "SNP (c)" hereinafter) is a polymorphism such that the underlined bases in brackets in SEQ ID NO: 18 are TA, for example. That is, for example, a tomato plant is resistant to root-knot nematodes when the underlined bases are TA, and is susceptible to root-knot nematodes when the underlined bases are other than TA (e.g., AC). The base sequence of SEQ ID NO: 18 can be obtained from the tomato plant deposited under Accession No. FERM BP-22251 to be described below, for example.

SEQ ID NO: 18
5'-AAGAAGGTGAATATT[TA]ACTGTATGATCCCCA-3'

The SNP (c) can be identified on the basis of known information in the database of the above-described web site etc., for example. The base sequence of SEQ ID NO: 9 is identical to the base sequence of Heinz except for the SNP (c), for example, and the underlined base in brackets is a polymorphism corresponding to the SNP (c). That is, for example, a tomato plant is resistant to root-knot nematodes when the underlined bases are TA, and is susceptible to root-knot nematodes when the underlined bases are other than TA (e.g., AC). Thus, the location of the SNP (c) can be identified on the basis of information on the known base sequence of Heinz, for example.

SEQ ID NO: 9
5'-TAACAAAAGGCAAATTAATGGGAACAAGGGACTGACATCAGGAG

CTTCCAAAGTCATATTTTAGGTCTTAGGCAAAGAAGGTGATAATT

[TA]ACTGTATGATCCCCATCAGGCCTTCAAAGACATTGCTAAAA-

3'

The YU06 (also referred to as "SNP (d)" hereinafter) is a polymorphism such that the underlined base in brackets in SEQ ID NO: 19 is C, for example. That is, for example, a tomato plant is resistant to root-knot nematodes when the underlined base is C, and is susceptible to root-knot nematodes when the underlined base is other than C (e.g., T). The base sequence of SEQ ID NO: 19 can be obtained from the tomato plant deposited under Accession No. FERM BP-22251 to be described below, for example.

SEQ ID NO: 19
5'-GGTAAGGATAGCTAAAGATATGGTGGAAAAGTGTAGAGGCTTACCTC

TTGCAAT[C]GTTGTATTGAGCGGACTACTTTCACATAAAAGGGGCTAG

ACCAATGGCAAAAAGTGAAAGATCACT-3'

The SNP (d) can be identified on the basis of known information in the database of the above-described web site etc., for example. The base sequence of SEQ ID NO: 10 is identical to the base sequence of Heinz except for the SNP (d), for example, and the underlined base in brackets is a polymorphism corresponding to the SNP (d). That is, for example, a tomato plant is resistant to root-knot nematodes when the underlined base is C, and is susceptible to root-knot nematodes when the underlined base is other than C (e.g., T). Thus, the location of the SNP (d) can be identified on the basis of information on the known base sequence of Heinz, for example.

SEQ ID NO: 10
5'-AGCTAAAGATATGGTGGAAAAGTGTAGAGGCTTACCTCTTGCAA

T[C]GTTGTATTGAGCGGACTACTTTCACATAAAAGGGGCTAGAC

CAATGGCAAAAAGTGAA-3

The YK66 (also referred to as "SNP (e)" hereinafter) is a polymorphism such that the underlined base in brackets in SEQ ID NO: 21 is C, for example. That is, for example, a tomato plant is resistant to root-knot nematodes when the underlined base is C, and is susceptible to root-knot nematodes when the underlined base is other than C (e.g., G). The base sequence of SEQ ID NO: 21 can be obtained from the tomato plant deposited under Accession No. FERM BP-22251 to be described below, for example.

SEQ ID NO: 21
5'-CTCAAACTCATTCAG[C]CAAAGACGTCTATCA-3'

The SNP (e) can be identified on the basis of known information in the database of the above-described web site etc., for example. The base sequence of SEQ ID NO: 12 is identical to the base sequence of Heinz except for the SNP (e), for example, and the underlined base in brackets is a polymorphism corresponding to the SNP (e). That is, for example, a tomato plant is resistant to root-knot nematodes when the underlined base is C, and is susceptible to root-knot nematodes when the underlined base is other than C (e.g., G). Thus, the location of the SNP (e) can be identified on the basis of information on the known base sequence of Heinz, for example.

SEQ ID NO: 12
5'-TATTCATGAACAAAAAACAGTGAGAAAAATGTGTCATACGACTC

AAACTCATTCAG[C]CAAAGACGTCTATCAATATTGTCCAGTTATT

AATAATAACTTTTTTTTTTTCTGTTTGC-3'

The TY38 (also referred to as, "SNP (f)" hereinafter) is a polymorphism such that the underlined base in brackets in SEQ ID NO: 22 is A, for example. That is, for example, a tomato plant is resistant to root-knot nematodes when the underlined base is A, and is susceptible to root-knot nematodes when the underlined base is other than A (e.g., C). The base sequence of SEQ ID NO: 22 can be obtained from the tomato plant deposited under Accession No. FERM BP-22251 to be described below, for example.

SEQ ID NO: 22
5'-CTAGACAACTCTTCTATTAG[A]ACACCATAAACAGAAAT

GTC-3'

The SNP (f) can be identified on the basis of known information in the database of the above-described web site etc., for example. The base sequence of SEQ ID NO: 2 is identical to the base sequence of Heinz except for the SNP (f), for example, and the underlined base in brackets is a polymorphism corresponding to the SNP (f). That is, for example, a tomato plant is resistant to root-knot nematodes when the underlined base is A, and is susceptible to root-knot nematodes when the underlined base is other than A (e.g., C). Thus, the location of the SNP (f) can be identified on the basis of information on the known base sequence of Heinz, for example.

SEQ ID NO: 2
5'-CGTACAGCTGCATAGCTTTCTCAATCTCCTTATTCCTAGACAAC

TCTTCTATTAG[A]ACGCCATAAACAGAAATGTCCAGCACAAAACC

CAATTTCTTCATTTTATCCAACAGTTGC-3'

The AR02 (also referred to as "SNP (g)" hereinafter) is a polymorphism such that the underlined base in brackets in SEQ ID NO: 23 is G, for example. That is, for example, a tomato plant is resistant to root-knot nematodes when the underlined base is G, and is susceptible to root-knot nematodes when the underlined base is other than G (e.g., A). The base sequence of SEQ ID NO: 23 can be obtained from the tomato plant deposited under Accession No. FERM BP-22251 to be described below, for example.

SEQ ID NO: 23
5'-GGCATTGACAGTGCT[G]ATGAAGATGATGAAA-3'

The SNP (g) can be identified on the basis of known information in the database of the above-described web site etc., for example. The base sequence of SEQ ID NO: 11 is identical to the base sequence of Heinz except for the SNP (g), for example, and the underlined base in brackets is a polymorphism corresponding to the SNP (g). That is, for example, a tomato plant is resistant to root-knot nematodes when the underlined base is G, and is susceptible to root-knot nematodes when the underlined base is other than G (e.g., A). Thus, the location of the SNP (g) can be identified on the basis of information on the known base sequence of Heinz, for example.

SEQ ID NO: 11
5'-GCTGTGCAATGACTTTTGCATTCAGGTCCTGGAACTTGGGGCAT

TGACAGTGCT[G]ATGAAGATGATGAAATCTCACACCACGGAAGAA

GCTGTAAAAGCATTATTT-3'

The HT12 (also referred to as "SNP (h)" hereinafter) is a polymorphism such that the underlined base in brackets in SEQ ID NO: 24 is C, for example. That is, for example, a tomato plant is resistant to root-knot nematodes when the underlined base is C, and is susceptible to root-knot nematodes when the underlined base is other than C (e.g., A). The base sequence of SEQ ID NO: 24 can be obtained from the tomato plant deposited under Accession No. FERM BP-22251 to be described below, for example.

SEQ ID NO: 24
5'-GAAAAGCACCTAGAGGAATAAAAAC[C]AATTGGATTATG

CACGAGTACCGCC-3'

The SNP (h) can be identified on the basis of known information in the database of the above-described web site etc., for example. The base sequence of SEQ ID NO: 7 is identical to the base sequence of Heinz except for the SNP (h), for example, and the underlined base in brackets is a polymorphism corresponding to the SNP (h). That is, for example, a tomato plant is resistant to root-knot nematodes when the underlined base is G, and is susceptible to root-knot nematodes when the underlined base is other than G (e.g., T). Thus, the location of the SNP (h) can be identified on the basis of information on the known base sequence of Heinz, for example. The base sequence of SEQ ID NO: 7 is the base sequence of a DNA strand complementary to a DNA strand including the base sequence of SEQ ID NO: 24, for example. That is, for example, G as SNP (h) in the SEQ ID NO: 7 is a base complementary to C as SNP (h) in the SEQ ID NO: 24.

SEQ ID NO: 7
5'-TTGCCAGCAGAGCGGTCCACGTTGGCGAGGCGGTACTCGTGCAT

AATCCAATT[G]GTTTTTATACCTCTGGGTGCTTTTCCGGCATAGA

ACACAAGTGCC-3'

The solcap_snp_sl_64250 (also referred to as "SNP (i)" hereinafter) is a polymorphism such that the underlined base in brackets in SEQ ID NO: 13 is G, for example. That is, for example, a tomato plant is resistant to root-knot nematodes when the underlined base is G, and is susceptible to root-knot nematodes when the underlined base is other than G (e.g., A). The base sequence of SEQ ID NO: 13 can be obtained from the tomato plant deposited under Accession No. FERM BP-22251 to be described below, for example.

SEQ ID NO: 13
5'-AGGGTTTGAAGACGA[G]GCAAGAATCTGGCAT-3'

The SNP (i) can be identified on the basis of known information in the database of the above-described web site etc., for example. The base sequence of SEQ ID NO: 3 is identical to the base sequence of Heinz except for the SNP (i), for example, and the underlined base in brackets is a polymorphism corresponding to the SNP (i). That is, for example, a tomato plant is resistant to root-knot nematodes when the underlined base is G, and is susceptible to root-knot nematodes when the underlined base is other than G (e.g., A). Thus, the location of the SNP (i) can be identified on the basis of information on the known base sequence of Heinz, for example.

SEQ ID NO: 3
5'-TTGGAGATCGGGTCAGCTTGTGTGCCACAGAGGAGAGGGTTTGA

AGACGA[G]GCAAGAATCTGGCATCTTATGCAACAAAAACCTTTAG

ATCAAGGGAAATT-3'

The solcap_snp_sl_21383 (also referred to as "SNP (j)" hereinafter) is a polymorphism such that the underlined base in brackets in SEQ ID NO: 14 is T, for example. That is, for example, a tomato plant is resistant to root-knot nematodes when the underlined base is T, and is susceptible to root-knot nematodes when the underlined base is other than T (e.g., A). The base sequence of SEQ ID NO: 14 can be obtained from the tomato plant deposited under Accession No. FERM BP-22251 to be described below, for example.

SEQ ID NO: 14
5'-ATTATAGTCTTACTT[T]AATGAATAAGCAACT-3'

The SNP (j) can be identified on the basis of known information in the database of the above-described web site etc., for example. The base sequence of SEQ ID NO: 4 is identical to the base sequence of Heinz except for the SNP (j), for example, and the underlined base in brackets is a polymorphism corresponding to the SNP (j). That is, for example, a tomato plant is resistant to root-knot nematodes when the underlined base is T, and is susceptible to root-knot nematodes when the underlined base is other than T (e.g., A). Thus, the location of the SNP (j) can be identified on the basis of information on the known base sequence of Heinz, for example.

SEQ ID NO: 4
5'-CGAAATGCTCTTTTTTCCTTTACACCATGTGACTGATTATAGTC

TTACTT[T]AATGAATAAGCAACTGAATACAAAAATTATCACCTCT

ATATAGATACAGT-3'

The solcap_snp_sl_21385 (also referred to as "SNP (k)" hereinafter) is a polymorphism such that the underlined base in brackets in SEQ ID NO: 16 is T, for example. That is, for example, a tomato plant is resistant to root-knot nematodes when the underlined base is T, and is susceptible to root-knot nematodes when the underlined base is other than T (e.g., C). The base sequence of SEQ ID NO: 16 can be obtained from the tomato plant deposited under Accession No. FERM BP-22251 to be described below, for example.

SEQ ID NO: 16
5'-AGAATCCTACGCCTGTAAATCTATCGACAAAAACCT[T]CTCATTG

ATTCCACCGACCGTGAGTGTCTCGATAAAGAACCC-3'

The SNP (k) can be identified on the basis of known information in the database of the above-described web site etc., for example. The base sequence of SEQ ID NO: 5 is identical to the base sequence of Heinz except for the SNP (k), for example, and the underlined base in brackets is a polymorphism corresponding to the SNP (k). That is, for example, a tomato plant is resistant to root-knot nematodes when the underlined base is T, and is susceptible to root-knot nematodes when the underlined base is other than T (e.g., C). Thus, the location of the SNP (k) can be identified on the basis of information on the known base sequence of Heinz, for example.

SEQ ID NO: 5
5'-TCTCCGGCGACCGGAGAATCCTACGCCTGTAAATCTATCGATAAAA

ACCT[T]CTCATTGATTCCACCGACCGTGAGTGTCTCGATAAAGAACCC

AAAATTCT-3'

The solcap_snp_sl_21390 (also referred to as "SNP (l)" hereinafter) is a polymorphism such that the underlined base in brackets in SEQ ID NO: 20 is T, for example. That is, for example, a tomato plant is resistant to root-knot nematodes when the underlined base is T, and is susceptible to root-knot nematodes when the underlined base is other than T (e.g., C). The base sequence of SEQ ID NO: 20 can be obtained from the tomato plant deposited under Accession No. FERM BP-22251 to be described below, for example.

```
                                          SEQ ID NO: 20
5'-GCAATATTTGGTTCC[T]TTAATCCCTCTTGG-3'
```

The SNP (l) can be identified on the basis of known information in the database of the above-described web site etc., for example. The base sequence of SEQ ID NO: 6 is identical to the base sequence of Heinz except for the SNP (l), for example, and the underlined base in brackets is a polymorphism corresponding to the SNP (l). That is, for example, a tomato plant is resistant to root-knot nematodes when the underlined base is T, and is susceptible to root-knot nematodes when the underlined base is other than T (e.g., C). Thus, the location of the SNP (l) can be identified on the basis of information on the known base sequence of Heinz, for example.

```
                                           SEQ ID NO: 6
5'-AGTGGCTTTATGCTCTACTAGGGAGCACGGGCGCTGCAATATTTG

GTTCC[T]TTAATCCCTCTTGGCCTATGTCATTGCATTGATTGTAACA

GCATATTAC-3'
```

Figure 2:
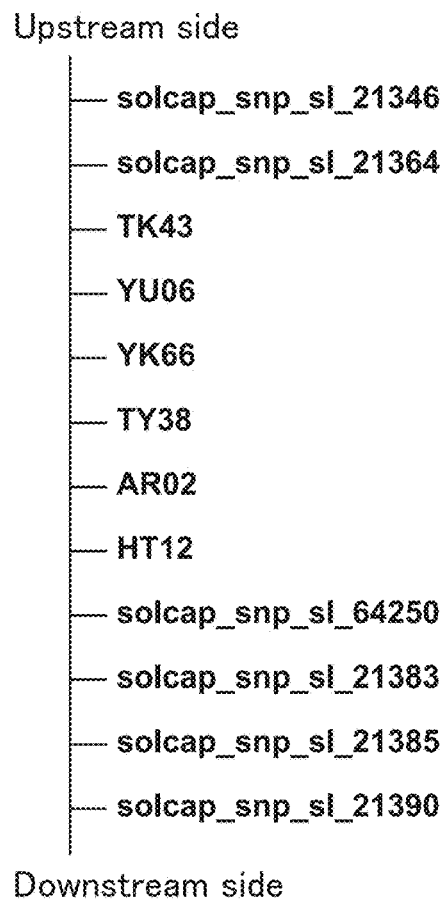
FIG. 2 is a schematic view showing relative chromosomal locations of SNP (single nucleotide polymorphism) markers.

The locations of the SNP markers on the chromosome are not particularly limited. For example, as shown in FIG. 2, on chromosome 4 of a tomato plant, the SNP markers are located in the following order from the upstream side (the solcap_snp_sl_21346 side) toward the downstream side (the solcap_snp_sl_21390 side): solcap_snp_sl_21346, solcap_snp_sl_21364, TK43, YU06, YK66, TY38, AR02, HT12, solcap_snp_sl_64250, solcap_snp_sl_21383, solcap_snp_sl_21385, and solcap_snp_sl_21390.

The number of the SNP markers present in the root-knot nematode resistance locus is not particularly limited. For example, the root-knot nematode resistance locus may include any one of the SNP markers or two or more of the SNP markers (i.e., two, three, four, five, six, seven, eight, nine, ten, or eleven selected from the SNP markers or all the twelve SNP markers). The relevance of these twelve kinds of polymorphisms (SNP markers) with the root-knot nematode resistance has not been reported heretofore. They are novel polymorphisms discovered first by the inventors of the present invention as being involved in the root-knot nematode resistance.

The combination of the SNP markers is not particularly limited, and examples thereof include the following combinations:
the combination of solcap_snp_sl_21346 and solcap_snp_sl_21364;
the combination of TK43 and YU06;
the combination of YK66, TY38, AR02, and HT12;
the combination of solcap_snp_sl_64250 and solcap_snp_sl_21383;
the combination of solcap_snp_sl_21385 and solcap_snp_sl_21390;
the combination of solcap_snp_sl_21346 and solcap_snp_sl_21390;
the combination of solcap_snp_sl_21346, TY38, and solcap_snp_sl_21390;
the combination of solcap_snp_sl_21364 and solcap_snp_sl_21385;
the combination of solcap_snp_sl_21364, TY38, and solcap_snp_sl_21385;
the combination of YU06 and solcap_snp_sl_64250; and
the combination of YU06, TY38, and solcap_snp_sl_64250.
Among the above combinations, the following combinations are preferable, for example, because they show higher correlation with the root-knot nematode resistance:
the combination of YK66, TY38, AR02, and HT12;
the combination of solcap_snp_sl_21346, TY38, and solcap_snp_sl_21390;
the combination of solcap_snp_sl_21364, TY38, and solcap_snp_sl_21385; and
the combination of YU06, TY38, and solcap_snp_sl_64250.

(2) Identification by Base Sequence Including SNP Marker

The root-knot nematode resistance locus may be specified by a base sequence including the SNP marker, as described in the above item (2), for example. The root-knot nematode resistance locus may consist of the base sequence or may include the base sequence, for example.

The base sequence including the SNP marker is not particularly limited, and examples thereof include the following polynucleotides (a) to (l). The polynucleotides (a) to (l) correspond to base sequences including the SNP markers, namely, the SNP (a) to the SNP (l), respectively.

The polynucleotide (a) is a base sequence including the SNP (a), i.e., solcap_snp_sl_21346, and examples thereof include the following polynucleotides (a1), (a2), and (a3). The polynucleotides (a2) and (a3) are polynucleotides each having a function equivalent to that of the polynucleotide (a1) regarding the root-knot nematode resistance in the root-knot nematode resistance locus.

(a1) a polynucleotide consisting of a base sequence of SEQ ID NO: 15

(a2) a polynucleotide consisting of a base sequence obtained by deletion, substitution, insertion, and/or addition of one or more bases excluding the 21st base (G) in the base sequence of the polynucleotide (a1)

(a3) a polynucleotide consisting of a base sequence having at least 80% identity to the base sequence of the polynucleotide (a1) with the 21st base (G) in the base sequence of the polynucleotide (a1) being conserved In the polynucleotide (a1), the underlined 21st base (G) in brackets in SEQ ID NO: 15 is a base corresponding to the polymorphism of the solcap_snp_sl_21346. The polynucleotide (a1) can be obtained from the tomato plant deposited under Accession No. FERM BP-22251 to be described below, for example.

In the polynucleotide (a2), the number of the one or more bases is, for example, 1 to 8, preferably 1 to 6, more preferably 1 to 5, still more preferably 1 to 3, and particularly preferably 1 or 2. In the present invention, the numerical range regarding the number of bases discloses, for example, all the positive integers falling within that range. That is, for example, the description "one to five bases" discloses all of "one, two, three, four, and five bases" (the same applies hereinafter).

In the polynucleotide (a3), the identity is, for example, at least 80%, preferably at least 85%, more preferably at least 89%, still more preferably at least 90%, particularly preferably at least 95%, at least 96%, at least 97%, at least 98%, or at least 99%. The identity can be determined by aligning two base sequences (the same applies hereinafter).

The polynucleotide (a1) may not only be, for example, a polynucleotide consisting of the base sequence of SEQ ID NO: 15, but also be, for example, a polynucleotide including the base sequence of SEQ ID NO: 15, i.e., a polynucleotide consisting of a base sequence of SEQ ID NO: 29. In the base sequence of SEQ ID NO: 29, a sequence indicated with capital letters corresponds to the base sequence of SEQ ID NO: 15, and the underlined 45th base in brackets is a base corresponding to the above-described polymorphism. In the case where the polynucleotide (a1) is a polynucleotide consisting of the base sequence of SEQ ID NO: 29, the phrase "21st base" regarding the polynucleotides (a2) and (a3) is replaced with "45th base".

SEQ ID NO: 29
5'-tcttcaactccgacttctgtaataCCAGAATTTATCGTGGTGGA[G]

GTTCTTGGAACTGCATGGAGgaaggttttaaccccagttcaat-3'

The polynucleotide (b) is a base sequence including the SNP (b), i.e., solcap_snp_sl_21364, and examples thereof include the following polynucleotides (b1), (b2), and (b3). The polynucleotides (b2) and (b3) are polynucleotides each having a function equivalent to that of the polynucleotide (b1) regarding the root-knot nematode resistance in the root-knot nematode resistance locus.

(b1) a polynucleotide consisting of a base sequence of SEQ ID NO: 17
(b2) a polynucleotide consisting of a base sequence obtained by deletion, substitution, insertion, and/or addition of one or more bases excluding the 16th base (T) in the base sequence of the polynucleotide (b1)
(b3) a polynucleotide consisting of a base sequence having at least 80% identity to the base sequence of the polynucleotide (b1) with the 16th base (T) in the base sequence of the polynucleotide (b1) being conserved In the polynucleotide (b1), the underlined 16th base (T) in brackets in SEQ ID NO: 17 is a base corresponding to the polymorphism of the solcap_snp_sl_21364. The polynucleotide (b1) can be obtained from the tomato plant deposited under Accession No. FERM BP-22251 to be described below, for example.

In the polynucleotide (b2), the number of the one or more bases is, for example, 1 to 6, preferably 1 to 5, more preferably 1 to 4, still more preferably 1 to 3, and particularly preferably 1 or 2.

In the polynucleotide (b3), the identity is, for example, at least 80%, preferably at least 85%, more preferably at least 89%, still more preferably at least 90%, particularly preferably at least 95%, at least 96%, at least 97%, at least 98%, or at least 99%.

The polynucleotide (b1) may not only be, for example, a polynucleotide consisting of the base sequence of SEQ ID NO: 17, but also be, for example, a polynucleotide including the base sequence of SEQ ID NO: 17, i.e., a polynucleotide consisting of a base sequence of SEQ ID NO: 31. In the base sequence of SEQ ID NO: 31, a sequence indicated with capital letters corresponds to the base sequence of SEQ ID NO: 17, and the underlined 48th base in brackets is a base corresponding to the above-described polymorphism. In the case where the polynucleotide (b1) is a polynucleotide consisting of the base sequence of SEQ ID NO: 31, the phrase "16th base" regarding the polynucleotides (b2) and (b3) is replaced with "48th base".

SEQ ID NO: 31
5'-tgaagaagcttgatcgagttggtgcccgccttGTTAGTAGCAATTCA

[T]GATGATCGATGGATCaatcaatcaatcaactatg-3'

The polynucleotide (c) is a base sequence including the SNP (c), i.e., TK43, and examples thereof include the following polynucleotides (c1), (c2), and (c3). The polynucleotides (c2) and (c3) are polynucleotides each having a function equivalent to that of the polynucleotide (c1) regarding the root-knot nematode resistance in the root-knot nematode resistance locus.

(c1) a polynucleotide consisting of a base sequence of SEQ ID NO: 18
(c2) a polynucleotide consisting of a base sequence obtained by deletion, substitution, insertion, and/or addition of one or more bases excluding the 16th base (T) and 17th base (A) in the base sequence of the polynucleotide (c1)
(c3) a polynucleotide consisting of a base sequence having at least 80% identity to the base sequence of the polynucleotide (c1) with the 16th base (T) and 17th base (A) in the base sequence of the polynucleotide (c1) being conserved In the polynucleotide (c1), the underlined 16th base (T) and 17th base (A) in brackets in SEQ ID NO: 18 are bases corresponding to the polymorphisms of the TK43. Also, the polynucleotide (c1) can be obtained from the tomato plant deposited under Accession No. FERM BP-22251 to be described below, for example.

In the polynucleotide (c2), the number of the one or more bases is, for example, 1 to 6, preferably 1 to 5, more preferably 1 to 4, still more preferably 1 to 3, and particularly preferably 1 or 2.

In the polynucleotide (c3), the identity is, for example, at least 80%, preferably at least 85%, more preferably at least 89%, still more preferably at least 90%, particularly preferably at least 95%, at least 96%, at least 97%, at least 98%, or at least 99%.

The polynucleotide (c1) may not only be, for example, a polynucleotide consisting of the base sequence of SEQ ID NO: 18, but also be, for example, a polynucleotide including the base sequence of SEQ ID NO: 18, i.e., a polynucleotide consisting of a base sequence of SEQ ID NO: 32. In the base sequence of SEQ ID NO: 32, a sequence indicated with capital letters corresponds to the base sequence of SEQ ID NO: 18, and the underlined 50th and 51st bases in brackets are bases corresponding to the above-described polymorphisms. In the case where the polynucleotide (c1) is a polynucleotide consisting of the base sequence of SEQ ID NO: 32, the phrase "16th and 17th bases" regarding the polynucleotides (c2) and (c3) is replaced with "50th and 51st bases".

SEQ ID NO: 32
5'-aatgggaacaagggactgacatcaggagcttccaAAGAAGGTGAATA

TT[TA]ACTGTATGATCCCCAtcaggccttcaaagacattgctaaaa-3'

The polynucleotide (d) is a base sequence including the SNP (d), i.e., YU06, and examples thereof include the following polynucleotides (d1), (d2), and (d3). The polynucleotides (d2) and (d3) are polynucleotides each having a function equivalent to that of the polynucleotide (d1) regarding the root-knot nematode resistance in the root-knot nematode resistance locus.

(d1) a polynucleotide consisting of a base sequence of SEQ ID NO: 19
(d2) a polynucleotide consisting of a base sequence obtained by deletion, substitution, insertion, and/or addition of one or more bases excluding the 55th base (C) in the base sequence of the polynucleotide (d1)
(d3) a polynucleotide consisting of a base sequence having at least 80% identity to the base sequence of the polynucleotide (d1) with the 55th base (C) in the base sequence of the polynucleotide (d1) being conserved In the polynucleotide (d1), the underlined 55th base (C) in brackets in SEQ ID NO: 19 is a base corresponding to the polymorphism of the YU06. The polynucleotide (d1) can be obtained from the tomato plant deposited under Accession No. FERM BP-22251 to be described below, for example.

In the polynucleotide (d2), the number of the one or more bases is, for example, 1 to 24, preferably 1 to 18, more preferably 1 to 13, still more preferably 1 to 12, 1 to 6, and particularly preferably 1, 2, or 3.

In the polynucleotide (d3), the identity is, for example, at least 80%, preferably at least 85%, more preferably at least 89%, still more preferably at least 90%, particularly preferably at least 95%, at least 96%, at least 97%, at least 98%, or at least 99%.

The polynucleotide (e) is a base sequence including the SNP (e), i.e., YK66, and examples thereof include the following polynucleotides (e1), (e2), and (e3). The polynucleotides (e2) and (e3) are polynucleotides each having a function equivalent to that of the polynucleotide (e1) regarding the root-knot nematode resistance in the root-knot nematode resistance locus.
(e1) a polynucleotide consisting of a base sequence of SEQ ID NO: 21
(e2) a polynucleotide consisting of a base sequence obtained by deletion, substitution, insertion, and/or addition of one or more bases excluding the 16th base (C) in the base sequence of the polynucleotide (e1)
(e3) a polynucleotide consisting of a base sequence having at least 80% identity to the base sequence of the polynucleotide (e1) with the 16th base (C) in the base sequence of the polynucleotide (e1) being conserved In the polynucleotide (e1), the underlined 16th base (C) in brackets in SEQ ID NO: 21 is a base corresponding to the polymorphism of the YK66. Also, the polynucleotide (e1) can be obtained from the tomato plant deposited under Accession No. FERM BP-22251 to be described below, for example.

In the polynucleotide (e2), the number of the one or more bases is, for example, 1 to 6, preferably 1 to 5, more preferably 1 to 4, still more preferably 1 to 3, and particularly preferably 1 or 2.

In the polynucleotide (e3), the identity is, for example, at least 80%, preferably at least 85%, more preferably at least 89%, still more preferably at least 90%, particularly preferably at least 95%, at least 96%, at least 97%, at least 98%, or at least 99%.

The polynucleotide (e1) may not only be, for example, a polynucleotide consisting of the base sequence of SEQ ID NO: 21, but also be, for example, a polynucleotide including the base sequence of SEQ ID NO: 21, i.e., a polynucleotide consisting of a base sequence of SEQ ID NO: 34. In the base sequence of SEQ ID NO: 34, a sequence indicated with capital letters corresponds to the base sequence of SEQ ID NO: 21, and the underlined 60th base in brackets is a base corresponding to the above-described polymorphism. In the case where the polynucleotide (e1) is a polynucleotide consisting of the base sequence of SEQ ID NO: 34, the phrase "16th base" regarding the polynucleotides (e2) and (e3) is replaced with "60th base".

SEQ ID NO: 34
5'-ttttattcatgaacaaaaaacagtgagaaaaatgtgtcatacgaCT

CAAACTCATTCAG[C]CAAAGACGTCTATCAatattgtccagttattaa taataacttttt-3'

The polynucleotide (f) is a base sequence including the SNP (f), i.e., TY38, and examples thereof include the following polynucleotides (f1), (f2), and (f3). The polynucleotides (f2) and (f3) are polynucleotides each having a function equivalent to that of the polynucleotide (f1) regarding the root-knot nematode resistance in the root-knot nematode resistance locus.
(f1) a polynucleotide consisting of a base sequence of SEQ ID NO: 22
(f2) a polynucleotide consisting of a base sequence obtained by deletion, substitution, insertion, and/or addition of one or more bases excluding the 21st base (A) in the base sequence of the polynucleotide (f1)
(f3) a polynucleotide consisting of a base sequence having at least 80% identity to the base sequence of the polynucleotide (f1) with the 21st base (A) in the base sequence of the polynucleotide (f1) being conserved In the polynucleotide (f1), the underlined 21st base (A) in brackets in SEQ ID NO: 22 is a base corresponding to the polymorphism of the TY38. The polynucleotide (f1) can be obtained from the tomato plant deposited under Accession No. FERM BP-22251 to be described below, for example.

In the polynucleotide (f2), the number of the one or more bases is, for example, 1 to 8, preferably 1 to 6, more preferably 1 to 5, still more preferably 1 to 4, 1 to 3, and particularly preferably 1 or 2.

In the polynucleotide (f3), the identity is, for example, at least 80%, preferably at least 85%, more preferably at least 89%, still more preferably at least 90%, particularly preferably at least 95%, at least 96%, at least 97%, at least 98%, or at least 99%.

The polynucleotide (f1) may not only be, for example, a polynucleotide consisting of the base sequence of SEQ ID NO: 22, but also be, for example, a polynucleotide including the base sequence of SEQ ID NO: 22, i.e., a polynucleotide consisting of a base sequence of SEQ ID NO: 25. In the base sequence of SEQ ID NO: 25, a sequence indicated with capital letters corresponds to the base sequence of SEQ ID NO: 22, and the underlined 34th base in brackets is a base corresponding to the above-described polymorphism.

In the case where the polynucleotide (f1) is a polynucleotide consisting of the base sequence of SEQ ID NO: 25, the phrase "21st base" regarding the polynucleotides (f2) and (f3) is replaced with "34th base".

SEQ ID NO: 25
5'-aatctccttattcCTAGACAACTCTTCTATTAG[A]ACACCATAAA

CAGAAATGTCcagcacaaaacccaatttcttcattttatc-3'

The polynucleotide (g) is a base sequence including the SNP (g), i.e., AR02, and examples thereof include the following polynucleotides (g1), (g2), and (g3). The polynucleotides (g2) and (g3) are polynucleotides each having a function equivalent to that of the polynucleotide (g1) regarding the root-knot nematode resistance in the root-knot nematode resistance locus.

(g1) a polynucleotide consisting of a base sequence of SEQ ID NO: 23
(g2) a polynucleotide consisting of a base sequence obtained by deletion, substitution, insertion, and/or addition of one or more bases excluding the 16th base (G) in the base sequence of the polynucleotide (g1)
(g3) a polynucleotide consisting of a base sequence having at least 80% identity to the base sequence of the polynucleotide (g1) with the 16th base (G) in the base sequence of the polynucleotide (g1) being conserved In the polynucleotide (g1), the underlined 16th base (G) in brackets in SEQ ID NO: 23 is a base corresponding to the polymorphism of the AR02. Also, the polynucleotide (g1) can be obtained from the tomato plant deposited under Accession No. FERM BP-22251 to be described below, for example.

In the polynucleotide (g2), the number of the one or more bases is, for example, 1 to 6, preferably 1 to 5, more preferably 1 to 4, still more preferably 1 to 3, and particularly preferably 1 or 2.

In the polynucleotide (g3), the identity is, for example, at least 80%, preferably at least 85%, more preferably at least 89%, still more preferably at least 90%, particularly preferably at least 95%, at least 96%, at least 97%, at least 98%, or at least 99%.

The polynucleotide (g1) may not only be, for example, a polynucleotide consisting of the base sequence of SEQ ID NO: 23, but also be, for example, a polynucleotide including the base sequence of SEQ ID NO: 23, i.e., a polynucleotide consisting of a base sequence of SEQ ID NO: 26. In the base sequence of SEQ ID NO: 26, a sequence indicated with capital letters corresponds to the base sequence of SEQ ID NO: 23, and the underlined 69th base in brackets is a base corresponding to the above-described polymorphism. When the polynucleotide (g1) is a polynucleotide consisting of the base sequence of SEQ ID NO: 26, the phrase "16th base" regarding the polynucleotides (g2) and (g3) is replaced with "69th base".

SEQ ID NO: 26
5'-gctattgtattgacgctgtgcaatgacttttgcattcaggtcctgga
acttggGGCATTGACAGTGCT[G]ATGAAGATGATGAAAtctcacacca
cagaagaagctgtaaaagcattatttgctatttcagcactaataaga-3'

The polynucleotide (h) is a base sequence including the SNP (h), i.e., HT12, and examples thereof include the following polynucleotides (h1), (h2), and (h3). The polynucleotides (h2) and (h3) are polynucleotides each having a function equivalent to that of the polynucleotide (h1) regarding the root-knot nematode resistance in the root-knot nematode resistance locus.
(h1) a polynucleotide consisting of a base sequence of SEQ ID NO: 24
(h2) a polynucleotide consisting of a base sequence obtained by deletion, substitution, insertion, and/or addition of one or more bases excluding the 26th base (C) in the base sequence of the polynucleotide (h1)
(h3) a polynucleotide consisting of a base sequence having at least 80% identity to the base sequence of the polynucleotide (h1) with the 26th base (C) in the base sequence of the polynucleotide (h1) being conserved In the polynucleotide (h1), the underlined 26th base (C) in brackets in SEQ ID NO: 24 is a base corresponding to the polymorphism of the HT12. The polynucleotide (h1) can be obtained from the tomato plant deposited under Accession No. FERM BP-22251 to be described below, for example.

In the polynucleotide (h2), the number of the one or more bases is, for example, 1 to 10, preferably 1 to 8, more preferably 1 to 6, still more preferably 1 to 5, 1 to 3, and particularly preferably 1 or 2.

In the polynucleotide (h3), the identity is, for example, at least 80%, preferably at least 85%, more preferably at least 89%, still more preferably at least 90%, particularly preferably at least 95%, at least 96%, at least 97%, at least 98%, or at least 99%.

The polynucleotide (h1) may not only be, for example, a polynucleotide consisting of a base sequence of SEQ ID NO: 24, but also be, for example, a polynucleotide including the base sequence of SEQ ID NO: 24, i.e., a polynucleotide consisting of a base sequence of SEQ ID NO: 27. In the base sequence of SEQ ID NO: 27, a sequence indicated with capital letters corresponds to the base sequence of SEQ ID NO: 24, and the underlined 50th base in brackets is a base corresponding to the above-described polymorphism. In the case where the polynucleotide (h1) is a polynucleotide consisting of the base sequence of SEQ ID NO: 27, the phrase "26th base" regarding the polynucleotides (h2) and (h3) is replaced with "50th base".

SEQ ID NO: 27
5'-agaaggcacttgtgttctatgccgGAAAAGCACCTAGAGGAATAAA
AAC[C]AATTGGATTATGCACGAGTACCGCC-3'

The polynucleotide (i) is a base sequence including the SNP (i), i.e., solcap_snp_sl_64250, and examples thereof include the following polynucleotides (i1), (i2), and (i3). The polynucleotides (i2) and (i3) are polynucleotides each having a function equivalent to that of the polynucleotide (i1) regarding the root-knot nematode resistance in the root-knot nematode resistance locus.
(i1) a polynucleotide consisting of a base sequence of SEQ ID NO: 13
(i2) a polynucleotide consisting of a base sequence obtained by deletion, substitution, insertion, and/or addition of one or more bases excluding the 16th base (G) in the base sequence of the polynucleotide (i1)
(i3) a polynucleotide consisting of a base sequence having at least 80% identity to the base sequence of the polynucleotide (i1) with the 16th base (G) in the base sequence of the polynucleotide (i1) being conserved In the polynucleotide (i1), the underlined 16th base (G) in brackets in SEQ ID NO: 13 is a base corresponding to the polymorphism of the solcap_snp_sl_64250. The polynucleotide (i1) can be obtained from the tomato plant deposited under Accession No. FERM BP-22251 to be described below, for example.

In the polynucleotide (i2), the number of the one or more bases is, for example, 1 to 6, preferably 1 to 5, more preferably 1 to 4, still more preferably 1 to 3, and particularly preferably 1 or 2.

In the polynucleotide (i3), the identity is, for example, at least 80%, preferably at least 85%, more preferably at least 89%, still more preferably at least 90%, particularly preferably at least 95%, at least 96%, at least 97%, at least 98%, or at least 99%.

The polynucleotide (i1) may not only be, for example, a polynucleotide consisting of the base sequence of SEQ ID NO: 13, but also be, for example, a polynucleotide including the base sequence of SEQ ID NO: 13, i.e., a polynucleotide consisting of a base sequence of SEQ ID NO: 28. In the base sequence of SEQ ID NO: 28, a sequence indicated with capital letters corresponds to the base sequence of SEQ ID NO: 13, and the underlined 25th base in brackets is a base corresponding to the above-described polymorphism. In the case where the polynucleotide (i1) is a polynucleotide consisting of a base sequence of SEQ ID NO: 28, the phrase "16th base" regarding the polynucleotides (i2) and (i3) is replaced with "25th base".

SEQ ID NO: 28
5'-acagaggagAGGGTTTGAAGACGA[G]GCAAGAATCTGGCATctt atgcaacaaaaacctta-3'

The polynucleotide (j) is a base sequence including the SNP (j), i.e., solcap_snp_sl_21383, and examples thereof include the following polynucleotides (j1), (j2), and (j3). The polynucleotides (j2) and (j3) are polynucleotides each having a function equivalent to that of the polynucleotide (j1) regarding the root-knot nematode resistance in the root-knot nematode resistance locus.

(j1) a polynucleotide consisting of a base sequence of SEQ ID NO: 14
(j2) a polynucleotide consisting of a base sequence obtained by deletion, substitution, insertion, and/or addition of one or more bases excluding the 16th base (T) in the base sequence of the polynucleotide (j1)
(j3) a polynucleotide consisting of a base sequence having at least 80% identity to the base sequence of the polynucleotide (j1) with the 16th base (T) in the base sequence of the polynucleotide (j1) being conserved In the polynucleotide (j1), the underlined 16th base (T) in brackets in SEQ ID NO: 14 is a base corresponding to the polymorphism of the solcap_snp_sl_21383. The polynucleotide (j1) can be obtained from the tomato plant deposited under Accession No. FERM BP-22251 to be described below, for example.

In the polynucleotide (j2), the number of the one or more bases is, for example, 1 to 6, preferably 1 to 5, more preferably 1 to 4, still more preferably 1 to 3, and particularly preferably 1 or 2.

In the polynucleotide (j3), the identity is, for example, at least 80%, preferably at least 85%, more preferably at least 89%, still more preferably at least 90%, particularly preferably at least 95%, at least 96%, at least 97%, at least 98%, or at least 99%.

The polynucleotide (j1) may not only be, for example, a polynucleotide consisting of the base sequence of SEQ ID NO: 14, but also be, for example, a polynucleotide including the base sequence of SEQ ID NO: 14, i.e., a polynucleotide consisting of a base sequence of SEQ ID NO: 33. In the base sequence of SEQ ID NO: 33, a sequence indicated with capital letters corresponds to the base sequence of SEQ ID NO: 14, and the underlined 35th base in brackets is a base corresponding to the above-described polymorphism. When the polynucleotide (j1) is a polynucleotide consisting of the base sequence of SEQ ID NO: 33, the phrase "16th base" regarding the polynucleotides (j2) and (j3) is replaced with "35th base".

SEQ ID NO: 33
5'-cctttacaccatgtgactgATTATAGTCTTACTT[T]AATGAATAA

GCAACTgaatacaaaaa-3'

The polynucleotide (k) is a base sequence including the SNP (k), i.e., solcap_snp_sl_21385, and examples thereof include the following polynucleotides (k1), (k2), and (k3). The polynucleotides (k2) and (k3) are polynucleotides each having a function equivalent to that of the polynucleotide (k1) regarding the root-knot nematode resistance in the root-knot nematode resistance locus.

(k1) a polynucleotide consisting of a base sequence of SEQ ID NO: 16
(k2) a polynucleotide consisting of a base sequence obtained by deletion, substitution, insertion, and/or addition of one or more bases excluding the 37th base (T) in the base sequence of the polynucleotide (k1)
(k3) a polynucleotide consisting of a base sequence having at least 80% identity to the base sequence of the polynucleotide (k1) with the 37th base (T) in the base sequence of the polynucleotide (k1) being conserved In the polynucleotide (k1), the underlined 37th base (T) in brackets in SEQ ID NO: 16 is a base corresponding to the polymorphism of the solcap_snp_sl_21385. The polynucleotide (k1) can be obtained from the tomato plant deposited under Accession No. FERM BP-22251 to be described below, for example.

In the polynucleotide (k2), the number of the one or more bases is, for example, 1 to 16, preferably 1 to 12, more preferably 1 to 9, still more preferably 1 to 8, 1 to 4, and particularly preferably 1, 2, or 3.

In the polynucleotide (k3), the identity is, for example, at least 80%, preferably at least 85%, more preferably at least 89%, still more preferably at least 90%, particularly preferably at least 95%, at least 96%, at least 97%, at least 98%, or at least 99%.

The polynucleotide (l) is a base sequence including the SNP (l), i.e., solcap_snp_sl_21390, and examples thereof include the following polynucleotides (l1), (l2), and (l3). The polynucleotides (l2) and (l3) are polynucleotides each having a function equivalent to that of the polynucleotide (l1) regarding the root-knot nematode resistance in the root-knot nematode resistance locus.

(l1) a polynucleotide consisting of a base sequence of SEQ ID NO: 20
(l2) a polynucleotide consisting of a base sequence obtained by deletion, substitution, insertion, and/or addition of one or more bases excluding the 16th base (T) in the base sequence of the polynucleotide (l1)
(l3) a polynucleotide consisting of a base sequence having at least 80% identity to the base sequence of the polynucleotide (l1) with the 16th base (T) in the base sequence of the polynucleotide (l1) being conserved In the polynucleotide (l1), the underlined 16th base (T) in brackets in SEQ ID NO: 20 is a base corresponding to the polymorphism of the solcap_snp_sl_21390. The polynucleotide (l1) can be obtained from the tomato plant deposited under Accession No. FERM BP-22251 to be described below, for example.

In the polynucleotide (l2), the number of the one or more bases is, for example, 1 to 6, preferably 1 to 5, more preferably 1 to 4, still more preferably 1 to 3, and particularly preferably 1 or 2.

In the polynucleotide (l3), the identity is, for example, at least 80%, preferably at least 85%, more preferably at least 89%, still more preferably at least 90%, particularly preferably at least 95%, at least 96%, at least 97%, at least 98%, or at least 99%.

The polynucleotide (l1) may not only be, for example, a polynucleotide consisting of the base sequence of SEQ ID NO: 20, but also be, for example, a polynucleotide including the base sequence of SEQ ID NO: 20, i.e., a polynucleotide consisting of a base sequence of SEQ ID NO: 30. In the base sequence of SEQ ID NO: 30, a sequence indicated with capital letters corresponds to the base sequence of SEQ ID NO: 20, and the underlined 21st base in brackets is a base corresponding to the above-described polymorphism. In the case where the polynucleotide (l1) is a polynucleotide consisting of the base sequence of SEQ ID NO: 30, the phrase "16th base" regarding polynucleotides (l2) and (l3) is replaced with "21st base".

SEQ ID NO: 30
5'-gcgctGCAATATTTGGTTCC[T]TTAATCCCCTCTTGGcctatgt cattgcattgattgtaa-3'

The number of base sequences including the SNP markers in the root-knot nematode resistance locus is not particularly limited. For example, the root-knot nematode resistance locus may include any one of the polynucleotides (a) to (l) or two or more of the polynucleotides (a) to (l) (i.e., two, three, four, five, six, seven, eight, nine, ten, or eleven selected from the polynucleotides (a) to (l) or all the twelve polynucleotides (a) to (l)).

The combination of the base sequences including the SNP markers is not particularly limited, and examples thereof include the following combinations:
the combination of the polynucleotides (a) and (b);
the combination of the polynucleotides (c) and (d);
the combination of the polynucleotides (i) and (j);
the combination of the polynucleotides (k) and (l);
the combination of the polynucleotides (e) to (h);
the combination of the polynucleotides (a) and (l);
the combination of the polynucleotides (a), (f), and (l);
the combination of the polynucleotides (b) and (k);
the combination of the polynucleotides (b), (f), and (k);
the combination of the polynucleotides (d) and (i); and
the combination of the polynucleotides (d), (f), and (i).
Among the above combinations, the following combinations are preferable, for example, because they show higher correlation with the root-knot nematode resistance:
the combination of the polynucleotides (e) to (h);
the combination of the polynucleotides (a), (f), and (l);
the combination of the polynucleotides (b), (f), and (k); and
the combination of the polynucleotides (d), (f), and (i).

(3) Identification by Base Sequence in Region between Sites of Two SNP Markers

The root-knot nematode resistance locus may be specified by the base sequence in a region between sites of two SNP markers, as described in the item (3), for example. The base sequence in a region between sites of the two SNP markers is not particularly limited, and examples thereof include a base sequence in a region between sites of two SNP markers selected from the group consisting of solcap_snp_sl_21346, solcap_snp_sl_21364, TK43, YU06, YK66, TY38, AR02, HT12, solcap_snp_sl_64250, solcap_snp_sl_21383, solcap_snp_sl_21385, and solcap_snp_sl_21390 on the chromosome.

The upstream-side end and the downstream-side end of the region can be identified by, for example, the sites of the two SNP markers, as described above. The region is not limited as long as it extends between the sites of the two SNP markers, for example. The region may or may not include both or one of the sites of the two SNP markers, for example. When the region includes the sites of the SNP markers, the upstream-side end and the downstream-side end of the region are the sites of the SNP markers. The bases at the upstream-side end and the downstream-side end may each be the above-described underlined base in the base sequence or may be a base other than the underlined base, for example.

The two SNP markers specifying the region are not particularly limited, and examples thereof include the following combinations:
the combination of solcap_snp_sl_21346 and TK43;
the combination of solcap_snp_sl_21364 and YK66;
the combination of YU06 and solcap_snp_sl_64250;
the combination of HT12 and solcap_snp_sl_21385;
the combination of solcap_snp_sl_21383 and solcap_snp_sl_21390;
the combination of solcap_snp_sl_21346 and solcap_snp_sl_21390; and
the combination of solcap_snp_sl_21364 and solcap_snp_sl_21385.
Among the above combinations, the following combinations are preferable, for example, because they show higher correlation with the root-knot nematode resistance:
the combination of YU06 and solcap_snp_sl_64250.

In the case where the root-knot nematode resistance locus is specified by the base sequence in a region between sites of the two SNP markers, it is preferable that, in the root-knot nematode resistance locus, the base sequence in the region includes the SNP marker(s) located in the region. Specifically, it is preferable that, in the root-knot nematode resistance locus, the base sequence in the region includes at least one SNP marker selected from the group consisting of solcap_snp_sl_21346, solcap_snp_sl_21364, TK43, YU06, YK66, TY38, AR02, HT12, solcap_snp_sl_64250, solcap_snp_sl_21383, solcap_snp_sl_21385, and solcap_snp_sl_21390, for example.

The SNP marker(s) located in the region may be, for example, one or both of the sites of the two SNP markers specifying the region on the chromosome, or may be the SNP marker(s) located between the sites of the two SNP markers specifying the region. The former also is referred to as a SNP marker at the end of the region, and the latter also is referred to as a SNP marker inside the region. The SNP markers located in the region may be both the SNP markers at the ends of the region and the SNP marker inside the region, for example.

The SNP marker(s) inside the region may be, for example, a SNP marker(s) located between the SNP marker on the upstream side and the SNP marker on the downstream side specifying the region, and can be determined as appropriate on the basis of the locations of the SNP markers shown in FIG. 2, for example. The number of the SNP markers between the sites of the two SNP markers may be one or more, for example. Specifically, for example, the SNP markers may be all the SNP markers located between the sites of the SNP markers specifying the region.

The combination of the base sequence in a region between sites of the two SNP markers and the SNP marker(s) in the base sequence in the region is not particularly limited, and examples thereof include the following conditions (i) to (v). Among them, the condition (i) is preferable, because it shows higher correlation with the root-knot nematode resistance.

Condition (i)

The root-knot nematode resistance locus includes a base sequence in a region between sites of YU06 and solcap_snp_sl_64250 on the chromosome, and
the base sequence in the region includes at least one SNP marker selected from the group consisting of YK66, TY38, AR02, and HT12.

Condition (ii)

The root-knot nematode resistance locus includes a base sequence in a region between sites of solcap_snp_sl_21364 and YK66 on the chromosome, and the base sequence in the region includes at least one of the SNP markers TK43 and YU06.

Condition (iii)

The root-knot nematode resistance locus includes a base sequence in a region between sites of HT12 and solcap_snp_sl_21385 on the chromosome, and the base sequence in the region includes at least one of the SNP markers solcap_snp_sl_64250 and solcap_snp_sl_21383.

Condition (iv)

The root-knot nematode resistance locus includes a base sequence in a region between sites of solcap_snp_sl_21346 and TK43 on the chromosome, and the base sequence in the region includes at least one of the SNP markers solcap_snp_sl_21346 and solcap_snp_sl_21364.

Condition (v)

The root-knot nematode resistance locus includes a base sequence in a region between sites of solcap_snp_sl_21383 and solcap_snp_sl_21390 on the chromosome, and the base sequence in the region includes at least one of the SNP markers solcap_snp_sl_21385 and solcap_snp_sl_21390.

In the condition (i), the number of the SNP markers inside the region is not particularly limited. For example, the SNP marker(s) inside the region may be any one of YK66, TY38, AR02, and HT12, or may be two or more (i.e., two, three, or four) of YK66, TY38, AR02, and HT12. In the case where the number of the SNP markers is two or more, the combination of the SNP markers is not particularly limited, and examples thereof include the following combinations.

Combination of Two SNP Markers:
the combination of YK66 and TY38;
the combination of YK66 and AR02;
the combination of YK66 and HT12;
the combination of TY38 and AR02;
the combination of TY38 and HT12; and
the combination of AR02 and HT12.

Combination of Three SNP Markers:
the combination of YK66, TY38, and AR02;
the combination of YK66, TY38, and HT12;
the combination of YK66, AR02, and HT12; and
the combination of TY38, AR02, and HT12.

Combination of Four SNP Markers:
the combination of YK66, TY38, AR02, and HT12.

In the condition (ii), the number of the SNP markers inside the region is not particularly limited. For example, the region may include either one or both of TK43 and YU06.

In the condition (iii), the number of SNP markers inside the region is not particularly limited. For example, the region may include either one or both of solcap_snp_sl_64250 and solcap_snp_sl_21383.

In the condition (iv), the number of SNP markers inside the region is not particularly limited. For example, the region may include either one or both of solcap_snp_sl_21346 and solcap_snp_sl_21364.

In the condition (v), the number of SNP markers inside the region is not particularly limited. For example, the region may include either one or both of solcap_snp_sl_21385 and solcap_snp_sl_21390.

For example, when the combination of the base sequence in a region between sites of the two SNP markers and the SNP marker(s) in the base sequence in the region is as specified by the condition (i), the root-knot nematode resistance locus may further satisfy at least one condition selected from the group consisting of the (ii) to (v). Examples of the combination of the conditions include the following combinations.

Two Conditions:
the combination of the condition (i) and either one of the condition (ii) to (v).

Three Conditions:
the combination of the condition (i), the condition (ii), and any one of the conditions (iii) to (v);
the combination of the condition (i), the condition (iii), and either one of the condition (iv) and the condition (v); and
the combination of the condition (i), the condition (iv), and the condition (v)

Four Conditions:
the combination of the condition (i), the condition (ii), the condition (iii), and either one of the condition (iv) and the condition (v); and
the combination of the condition (i), the condition (iv) the condition (v), and either one of the condition (ii) and the condition (iii).

Five Conditions:
the combination of the condition (i), the condition (ii), the condition (iii), the condition (iv), and the condition (v).

The root-knot nematode resistance marker according to the present invention can confer root-knot nematode resistance to tomato plants, for example. In the present invention, the degree of the root-knot nematode resistance of a tomato plant can be expressed by the severity (the root gall severity) according to the method described in the following literature, for example. Regarding the calculation of the severity according to this method, explanation in Example 1 to be described below can be referred to, and the root gall severity of 1 or less can be evaluated as being resistant to root-knot nematodes and the root gall severity of 2 or more can be evaluated as being susceptible to root-knot nematodes, for example.

Literature: Satoshi AIBA et al., Sentyu-gaku Jikken-hou (Experimental Techniques in Nematology), (2004), pp. 103 to 105

2. Root-knot Nematode Resistant Tomato Plant

As described above, the root-knot nematode resistant tomato plant according to the present invention includes a root-knot nematode resistance locus on chromosome 4. The root-knot nematode resistant tomato plant of the present invention is characterized in that it includes a root-knot nematode resistance locus on chromosome 4, and other configurations and conditions are not particularly limited. The root-knot nematode resistant tomato plant of the present invention includes the root-knot nematode resistance marker of the present invention, which includes the root-knot nematode resistance locus. Thus, the above description regarding the root-knot nematode resistance marker for tomato plants according to the present invention is applicable to the root-knot nematode resistant tomato plant according to the present invention, for example. In the present invention, the root-knot nematode resistance locus on chromosome 4 should be interpreted as interchangeable with the root-knot nematode resistance marker according to the present invention, for example.

The root-knot nematode resistant tomato plant according to the present invention is resistant to root-knot nematodes.

In the root-knot nematode resistant tomato plant of the present invention, the root-knot nematode resistance is conferred by the root-knot nematode resistance locus on chromosome 4. Although the root-knot nematode resistant tomato plant of the present invention has the root-knot nematode resistance locus on chromosome 4, it may have the root-knot nematode resistance locus on chromosome 4 on, instead of chromosome 4, any chromosome other than chromosome 4, for example. That is, the root-knot nematode resistant tomato plant of the present invention may have the root-knot nematode resistance locus on chromosome 4 on, for example, any of chromosome 1, chromosome 2, chromosome 3, chromosome 5, chromosome 6, chromosome 7, chromosome 8, chromosome 9, chromosome 10, chromosome 11, and chromosome 12.

In the root-knot nematode resistant tomato plant of the present invention, the description regarding the root-knot nematode resistance locus provided above in connection with the root-knot nematode resistance marker for tomato plants according to the present invention is applicable to the root-knot nematode resistance locus in the root-knot nematode resistant tomato plant of the present invention, for example.

The root-knot nematode resistance of the root-knot nematode resistant tomato plant according to the present invention can function at growth temperatures in the range from 8° C. to 40° C., for example. That is, the root-knot nematode resistance of the root-knot nematode resistant tomato plant according to the present invention can function even at growth temperatures at which the root-knot nematode resistance conferred by a conventional resistance gene such as Mi-1 cannot function, e.g., 28° C. or higher, specifically 30° C. to 35° C.

The root-knot nematode resistant tomato plant of the present invention may be, for example, the tomato plant deposited under Accession No. FERM BP-22251 (*S. lycopersicum*) or a progeny line thereof. The information on the deposit is as follows.
Type of deposit: International deposit
Name of depository institution: National Institute of Technology and Evaluation; NITE-IPOD
Address: 2-5-8-120, Kazusakamatari, Kisarazu-shi, Chiba 292-0818, Japan
Accession No. FERM BP-22251
Identifying designation: Takii3
Date of acceptance: May 8, 2013

The root-knot nematode resistant tomato plant according to the present invention can be produced by, for example, introducing the root-knot nematode resistance locus to a tomato plant. The method for introducing the root-knot nematode resistance locus to a tomato plant is not particularly limited, and a conventionally known genetic engineering procedure may be used, for example. The root-knot nematode resistance locus to be introduced may be the above-described root-knot nematode resistance locus, for example.

The characteristics of the root-knot nematode resistant tomato plant of the present invention other than the root-knot nematode resistance, such as, for example, morphological characteristics and biological characteristics, are not particularly limited.

The root-knot nematode resistant tomato plant of the present invention may also have any other resistance.

The term "plant body" as used in the present invention may refer to either a plant individual representing the whole plant or a part of the plant individual. The part of the plant individual may be any of organs, tissues, cells, and propagules, for example. Examples of the organs include petals, corollas, flowers, leaves, seeds, fruits, stems, and roots. The tissue is a part of the organ, for example. The part of the plant body may be one kind of organ, tissue, and/or cell, or two or more kinds of organs, tissues, and/or cells, for example.

3. Method for Producing Root-knot Nematode Resistant Tomato Plant

Next, the method for producing a root-knot nematode resistant tomato plant according to the present invention (also referred to simply as "production method" hereinafter) will be described. The methods to be described below are merely illustrative, and the present invention is by no means limited to these methods. In the present invention, the production method also can be referred to as "growing method", for example. Also, in the present invention, the root-knot nematode resistance locus should be interpreted as interchangeable with the root-knot nematode resistance marker according to the present invention.

As described above, the method for producing a root-knot nematode resistant tomato plant according to the present invention includes the following steps (a) and (b):
(a) crossing the root-knot nematode resistant tomato plant according to the present invention with another tomato plant; and
(b) selecting a root-knot nematode resistant tomato plant from one or more tomato plants obtained in the step (a) or progeny lines thereof.

The production method according to the present invention is characterized in that the root-knot nematode resistant tomato plant according to the present invention is used as a parent, and other steps and conditions are by no means limited. The above description regarding the root-knot nematode resistant tomato plant according to the present invention etc. is applicable to the production method of the present invention, for example.

In the step (a), a root-knot nematode resistant tomato plant used as a first parent is not limited as long as it is the root-knot nematode resistant tomato plant of the present invention. The root-knot nematode resistant tomato plant preferably is the above-described tomato plant deposited under Accession No. FERM BP-22251 or a progeny line thereof, for example. In the step (a), the root-knot nematode resistant tomato plant used as the first parent also can be obtained by the screening method of the present invention to be described below, for example. Thus, it is possible to provide the root-knot nematode resistant tomato plant by, for example, selecting it from one or more tomato plants to be examined (also referred to as "candidate tomato plants") by the following step (x) prior to the step (a), for example: (x) selecting the root-knot nematode resistant tomato plant of the present invention from one or more tomato plants to be examined.

In the step (x), the selection of the root-knot nematode resistant tomato plant can be referred to as selection of the tomato plant including a root-knot nematode resistance locus. Thus, the step (x) can be carried out by the following steps (x1) and (x2), for example.
(x1) detecting the presence or absence of the root-knot nematode resistance locus on a chromosome of each of the one or more tomato plants to be examined; and
(x2) selecting one or more tomato plants to be examined having the root-knot nematode resistance locus as a root-knot nematode resistant tomato plant.

As described above, the selection in the step (x) is selection of the tomato plant including a root-knot nematode resistance locus, for example. Specifically, the root-knot nematode resistant tomato plant can be selected by carrying out detection of the root-knot nematode resistance locus with respect to the one or more tomato plants to be examined. As described above in connection with the root-knot nematode resistance marker of the present invention, the root-knot nematode resistance locus can be detected by using, for example, any of the following (1) to (3) specifying the root-knot nematode resistance locus or any combination thereof (1) the SNP marker; (2) a base sequence including the SNP marker; and (3) a base sequence in a region between sites of two SNP markers.

The selection in the step (x) will be described with reference to the following specific example. It is to be noted, however, that the present invention is not limited thereto. The description regarding the root-knot nematode resistance locus provided above in connection with the root-knot nematode resistance marker of the present invention is applicable to the root-knot nematode resistance locus in the production method of the present invention.

(1) Identification by SNP Marker

The selection in the step (x) is, for example, selection of a tomato plant including a root-knot nematode resistance locus identified by at least one SNP marker selected from the group consisting of solcap_snp_sl_21346, solcap_snp_sl_21364, TK43, YU06, YK66, TY38, AR02, HT12, solcap_snp_sl_64250, solcap_snp_sl_21383, solcap_snp_sl_21385, and solcap_snp_sl_21390. The SNP marker to be selected is not particularly limited, and the explanation in the "(1) Identification by SNP marker" provided above in connection with the root-knot nematode resistance marker of the present invention is applicable, for example.

As a specific example, the selection in the step (x) may be selection of a tomato plant including a root-knot nematode resistance locus identified by at least one SNP marker selected from the group consisting of YK66, TY38, AR02, and HT12, for example.

(2) Identification by Base Sequence Including SNP Marker

The selection in the step (x) is, for example, selection of a tomato plant including a root-knot nematode resistance locus identified by at least one polynucleotide selected from the group consisting of the polynucleotides (a) to (l). Regarding the polynucleotides (a) to (l), the explanation in the "(2) Identification by base sequence including SNP marker" provided above in connection with the root-knot nematode resistance marker of the present invention is applicable, for example.

As a specific example, the selection in the step (x) may be selection of a tomato plant including a root-knot nematode resistance locus identified by at least one polynucleotide selected from the group consisting of the polynucleotides (e) to (h), for example.

(3) Identification by Base Sequence in Region between Sites of Two SNP Markers

The selection in the step (x) is, for example, selection of a tomato plant including a root-knot nematode resistance locus that includes a base sequence in a region between sites of two SNP markers selected from the group consisting of solcap_snp_sl_21346, solcap_snp_sl_21364, TK43, YU06, YK66, TY38, AR02, HT12, solcap_snp_sl_64250, solcap_snp_sl_21383, solcap_snp_sl_21385, and solcap_snp_sl_21390 on the chromosome. Regarding the base sequence in a region between sites of the two SNP markers, the explanation in the "(3) Identification by base sequence in region between sites of two SNP markers" provided above in connection with the root-knot nematode resistance marker of the present invention is applicable, for example.

As a specific example, the selection in the step (x) is selection of a tomato plant including a root-knot nematode resistance locus in which the base sequence in the region includes at least one SNP marker selected from the group consisting of solcap_snp_sl_21346, solcap_snp_sl_21364, TK43, YU06, YK66, TY38, AR02, HT12, solcap_snp_sl_64250, solcap_snp_sl_21383, solcap_snp_sl_21385, and solcap_snp_sl_21390, for example.

Also, the selection in the step (x) may be selection of a tomato plant including a root-knot nematode resistance locus satisfying the condition (i), for example.

Also, the selection in the step (x) may be selection of a tomato plant including a root-knot nematode resistance locus further satisfying at least one condition selected from the group consisting of the conditions (ii) to (v), for example.

The chromosome to be subjected to the detection of the presence or absence of the root-knot nematode resistance locus preferably is chromosome 4.

In the step (a), a tomato plant to be used as the other parent is not particularly limited, and may be, for example, a tomato plant carrying a known root-knot nematode resistance gene, a tomato plant having any other resistance, or the root-knot nematode resistant tomato plant of the present invention.

In the step (a), the method for crossing the root-knot nematode resistant tomato plant with another tomato plant is not particularly limited, and a known method can be employed.

In the step (b), tomato plants from which a root-knot nematode resistant tomato plant is to be selected may be the tomato plants obtained in the step (a) or progeny lines obtained from these tomato plants, for example. Specifically, for example, the tomato plants from which a root-knot nematode resistant tomato plant is to be selected may be the F1 tomato plants obtained by the crossing in the step (a) or their progeny lines. The progeny line may be a selfed progeny or a backcross progeny of the F1 tomato plant obtained by the crossing in the step (a), or may be a tomato plant obtained by crossing the F1 tomato plant with another tomato plant, for example.

In the step (b), the selection of a root-knot nematode resistant tomato plant can be achieved by, for example, examining the root-knot nematode resistance directly or indirectly.

In the step (b), the direct examination can be conducted by evaluating the root-knot nematode resistance of the obtained F1 tomato plant or a progeny line thereof on the basis of the above-described severity, for example. Specifically, for example, the direct examination can be conducted by inoculating the F1 tomato plant or the progeny line thereof with root-knot nematodes and evaluating the root-knot nematode resistance on the basis of the severity. In this case, for example, the F1 tomato plant or the progeny line showing the severity of 1 or less can be selected as a root-knot nematode resistant tomato plant.

In the step (b), the selection by the indirect examination can be achieved by the following steps (b1) and (b2), for example:

(b1) detecting the presence or absence of a root-knot nematode resistance locus on a chromosome of each of the tomato plants obtained in the step (a) or progeny lines thereof, and (b2) selecting the tomato plants obtained in the step (a) or progeny lines thereof having the root-knot nematode resistance locus as a root-knot nematode resistant tomato plant.

The selection of the root-knot nematode resistant tomato plant in the step (b) can be performed in the same manner as in the step (x), namely, by detecting the presence or absence of the root-knot nematode resistance locus, for example. More specifically, the selection can be performed by detecting the presence or absence of the root-knot nematode resistance locus using the molecular marker.

The production method of the present invention preferably further includes growing the root-knot nematode resistant tomato plant selected in the step (b).

The tomato plant or the progeny line demonstrated to be root-knot nematode resistant in the above-described manner can be selected as the root-knot nematode resistant tomato plant.

The production method of the present invention further may include the step of collecting seeds from the progeny line obtained from the line obtained by the crossing.

4. Screening Method for Root-knot Nematode Resistant Tomato Plant

As described above, the screening method for a root-knot nematode resistant tomato plant according to the present invention (also referred to simply as "screening method" hereinafter) includes the step of as a parent for producing a root-knot nematode resistant tomato plant by crossing, selecting a tomato plant including, as a root-knot nematode resistance marker for a tomato plant, a root-knot nematode resistance locus on chromosome 4 from one or more tomato plants to be examined.

The screening method of the present invention is characterized in that it includes the step of selecting a plant including, as a root-knot nematode resistance marker for a tomato plant, a root-knot nematode resistance locus on chromosome 4 from one or more tomato plants to be examined, and other steps and conditions are by no means limited. According to the screening method of the present invention, a root-knot nematode resistant parent can be obtained by using the root-knot nematode resistance marker of the present invention. The above description regarding the root-knot nematode resistance marker for tomato plants according to the present invention etc. is applicable to the screening method of the present invention, for example.

As to the selection of the parent, the explanation of the step (x) provided above in connection with the method for producing a root-knot nematode resistant tomato plant according to the present invention is applicable, for example.

EXAMPLES

The present invention will be described specifically below with reference to examples. It is to be noted, however, that the present invention is by no means limited to embodiments described in the following examples.

[Example 1]

The present example analyzed the mode of inheritance of the root-knot nematode resistance locus in a novel root-knot nematode resistant tomato plant.

In order to develop a novel tomato plant resistant to root-knot nematodes, a large amount of seeds collected from tomato lines obtained by subculture breeding in a farm owned by TAKII & CO., LTD. were subjected to breeding, and the root-knot nematode resistance of the resultant tomato lines was examined. As a result, a novel root-knot nematode resistance tomato line (*S. lycopersicum*) exhibiting root-knot nematode resistance at a temperature of 28° C. or higher was obtained. This novel root-knot nematode resistant tomato plant was deposited under Accession No. FERM BP-22251. Hereinafter, this root-knot nematode resistant tomato plant is referred to as the "deposited line".

A tomato plant of the deposited line (Accession No. FERM BP-22251) was crossed with a root-knot nematode susceptible tomato plant "Vespa (TAKII & CO., LTD., *S. lycopersicum*)", whereby an F2 segregating population made up of 141 individuals (also referred to as "141 lines" hereinafter) was obtained. Also, a tomato plant of the deposited line was crossed with a root-knot nematode susceptible tomato plant "Kagemusha (TAKII & CO., LTD., *S. lycopersicum*)", whereby an F2 segregating population made up of 70 individuals (also referred to as "70 lines" hereinafter) was obtained. Vespa and Kagemusha are each a complex root-knot nematode resistant rootstock that carries a root-knot nematode resistance gene Mi-1 but is susceptible to root-knot nematodes at a temperature of 28° C. or higher. The 141 lines and the 70 lines were subjected to a root-knot nematode inoculation test to be described below. Also, as control plots, populations each made up of 20 individuals obtained from Helper-M (TAKII & CO., LTD., *S. lycopersicum*), Anchor-T (TAKII & CO., LTD., *S. lycopericum*), Kagemusha, Vespa, Moneymaker (*S. lycopersicum*), and the tomato plant of the deposited line were used. Helper-M and Anchor-T are each a complex root-knot nematode resistant rootstock that carries a root-knot nematode resistance gene Mi-1 but is susceptible to root-knot nematodes at a temperature of 28° C. or higher. Moneymaker is a scion that does not carry Mi-1 and is susceptible to root-knot nematodes.

The root-knot nematode inoculation test was performed in the following manner on the basis of the method described in the literature "Sentyu-gaku Jikken-hou (Experimental Techniques in Nematology) published on Mar. 25, 2004 (The Japanese Nematological Society)".

As the root-knot nematodes, those derived from a single southern root-knot nematode egg mass collected from a tomato cultivation greenhouse in Yamanashi prefecture were used. First, sterilized soil was placed in cultivation cups, and two individuals of root-knot nematode-free tomato seedlings were grown for 30 days in an incubator set at 30° C.±1° C. Then, in the soil around the root of each tomato seedling grown for 30 days, three inoculation holes each having a diameter of 10 mm and a depth of 20 mm were formed with a glass rod. Thereafter, the root-knot nematodes were suspended in clarified water at a density of 200 root-knot nematodes/mL. 1 mL of the root-knot nematode suspension was aspirated with a Komagome pipette, and inoculation was achieved by supplying the suspension to these inoculation holes (1 mL/hole). The seedlings were further grown under the same conditions. After a lapse of 40 days from the inoculation, roots were collected from the grown individuals, washed with water, and the disease investigation was performed in the following manner.

The disease investigation was carried out on the basis of the method described in Non-Patent Document 4. As disease indices, the degree of root galls was evaluated in accordance with the following criteria.

Root gall severity 0: There is no root gall.
Root gall severity 1: There are a few root galls, but there is no notable damage.
Root gall severity 2: The presence of root galls is apparent. However, there are only a few large root galls and/or linked root galls.
Root gall severity 3: Many large and small root galls are observed. Some of the roots are covered with root galls and become swollen, but the proportion of root galls is not more than 50% of the entire root region.

Root gall severity 4: Most of the roots are covered with root galls and become swollen.

The result of the disease investigation is shown in Table 1. As can be seen in Table 1, among the 141 lines, the root gall severity was not more than 1 in 105 individuals, which accounted for 74% of all the individuals. On the other hand, among the 70 lines, the root gall severity was not more than 1 in 50 individuals, which accounted for 71% of all the individuals. From the correlation of the root gall severity in the 141 lines and the 70 lines with the frequencies of appearance of these individuals, it was found that the mode of inheritance of the root-knot nematode resistance in the deposited line is unifactorial dominant. Also, Helper-M, Anchor-T, Kagemusha, and Vespa each carrying Mi-1 and Moneymaker not carrying Mi-1 were subjected to the test under the same conditions. As a result, it was demonstrated that they exhibit root-knot nematode susceptibility depending on a growth condition of 30° C.±1° C., whereas the deposited line is resistant to root-knot nematodes. As evaluation criteria for root gall severity, the photograph of FIG. 1 shows representative examples of an individual exhibiting the root gall severity of 0 and an individual exhibiting the root gall severity of 4.

Literature: Blanca J, Cañizares J, Cordero L, Pascual L, Diez M J, et al. (2012) Variation Revealed by SNP Genotyping and Morphology Provides Insight into the Origin of the Tomato. PLoS ONE 7(10)

Also, by web retrieval utilizing tomato genome sequences available to the public on the web site of the SOL Genomics Network (solgenomics.net/), the polymorphisms present uniquely in both the parents, i.e., the root-knot nematode resistant tomato plant (the deposited line) and the root-knot nematode susceptible tomato plant (Moneymaker), were identified. Furthermore, in the F2 segregating population, polymorphisms seen in individuals carrying the polymorphisms in homozygous form and individuals carrying the polymorphisms in heterozygous form were identified as SNP markers. Then, using the thus-identified SNP markers, the linkage analysis was conducted in the same manner.

As a result, on chromosome 4, one region with high correlation with the root gall severity was identified. The region includes SNPs identified by the following SNP markers: solcap_snp_sl_21346, solcap_snp_sl_21364, TK43, YU06, YK66, TY38, AR02, HT12, solcap_snpsl_64250, solcap_snp_sl_21383, solcap_snp_sl_21385, and solcap_snp_sl_21390. This result

TABLE 1

| | Root gall severity | | | | | Total number of individuals | Proportion of individuals with root gall severity of 1 or less |
|---|---|---|---|---|---|---|---|
| | 0 | 1 | 2 | 3 | 4 | | |
| F2 segregating population (141 lines) | 101 individuals | 4 individuals | 3 individuals | 8 individuals | 25 individuals | 141 individual | 74% |
| F2 segregating population (70 lines) | 35 individuals | 15 individuals | 0 individuals | 19 individuals | 1 individual | 70 individuals | 71% |
| Deposited line | 17 individuals | 3 individuals | 0 individuals | 0 individuals | 0 individuals | 20 individuals | 100% |
| Helper-M | 0 individuals | 0 individuals | 2 individuals | 1 individual | 17 individuals | 20 individuals | 0% |
| Anchor-T | 0 individuals | 0 individuals | 1 individual | 0 individuals | 19 individuals | 20 individuals | 0% |
| Kagemusha | 0 individuals | 0 individuals | 1 individual | 4 individuals | 15 individuals | 20 individuals | 0% |
| Vespa | 0 individuals | 0 individuals | 2 individuals | 2 individuals | 16 individuals | 20 individuals | 0% |
| Moneymaker | 0 individuals | 0 individuals | 0 individuals | 0 individuals | 20 individuals | 20 individuals | 0% |

[Example 2]

The present example carried out identification of a novel root-knot nematode resistance locus with respect to the 141 lines in the F2 segregating population obtained in Example 1.

DNAs extracted from the 141 lines were subjected to genotyping according to the SOLCAP SNP assay (see the following literatures). Thereafter, linkage maps were prepared using software (Join Map), and linkage analysis was conducted using software (Win QTL cartographer).

Literature: Hamilton J P, Sim S C, Stoffel K, Van Deynze A, Buell C R, et al. (2012) Single Nucleotide Polymorphism Discovery in Cultivated Tomato via Sequencing by Synthesis. The Plant Genome 5.

Literature: Sim S-C, Durstewitz G, Plieske J, Wieseke R, Ganal M W, et al. (2012) Development of a Large SNP Genotyping Array and Generation of High-Density Genetic Maps in Tomato. PLoS ONE 7(7)

revealed that a novel root-knot nematode resistance locus is located on chromosome 4. As described above, the known root-knot nematode resistance loci are located on chromosome 6 and chromosome 12. Thus, it was revealed that the root-knot nematode gene locus of the present invention is a novel resistance gene locus different from the known resistance gene loci.

[Example 3]

96 individuals (also referred to as "96 lines" hereinafter) in an F2 segregating population were newly obtained in the same manner as for the 141 lines in Example 1. Then, with respect to the thus-obtained 96 lines, SNP assay was conducted in the same manner as in Example 2 to identify the bases corresponding to the polymorphisms of the SNP markers, solcap_snp_sl_21346, solcap_snp_sl_21364, TK43, YU06, YK66, TY38, AR02, HT12, solcap_snp_sl_64250, solcap_snp_sl_21383, solcap_snp_sl_21385, and solcap_snp_sl_21390. Furthermore, with respect to these individuals, the root-knot nematode inoculation test was performed in the same manner as in Example 1. The results thereof are shown in Table 2. In Table 2, "resistant homo" indicates an individual carrying the SNP markers in resistant-type homozygous form; "hetero" indicates an individual carrying the SNP markers in heterozygous form; and "susceptible homo" indicates an individual carrying the SNP markers in susceptible-type homozygous form. As can be seen in Table 2, the individuals indicated as "resistant homo" and "hetero" all exhibited the root gall severity of 1 or less. This demonstrates that the SNP markers are responsible for the root-knot nematode resistance.

[Example 4]

62 individuals (also referred to as "62 lines" hereinafter) in an F2 segregating population were newly obtained in the same manner as for the 70 lines in Example 1. Then, with respect to the thus-obtained 62 lines, SNP assay was conducted in the same manner as in Example 2 to identify the bases corresponding to the polymorphisms of the SNP markers, solcap_snp_sl_21346, solcap_snp_sl_21364, TK43, YU06, YK66, TY38, AR02, HT12, solcap_snp_sl_64250, solcap_snp_sl_21383, solcap_snp_sl_21385, and solcap_snp_sl_21390. Furthermore, with respect to these individuals, the root-knot nematode

TABLE 2

| | Root gall severity | | | | | Total number of individuals | Proportion of individuals with root gall severity of 1 or less |
|---|---|---|---|---|---|---|---|
| | 0 | 1 | 2 | 3 | 4 | | |
| Resistant homo | 22 individuals | 3 individuals | 0 individuals | 0 individuals | 0 individuals | 25 individuals | 100% |
| Hetero | 40 individuals | 5 individuals | 0 individuals | 0 individuals | 0 individuals | 45 individuals | 100% |
| Susceptible homo | 0 individuals | 0 individuals | 1 individual | 6 individuals | 19 individuals | 26 individuals | 0% |

Next, from the 96 lines in the F2 segregating population, three individuals carrying the SNP markers in resistant-type homozygous form and three individuals carrying the SNP markers in susceptible-type homozygous form were selected. They were self-crossed, and seeds were obtained from the thus-obtained 6 lines in the F3 population.

Using the seeds from the 6 lines in the F3 population, 10 individuals were obtained from each line. Then, in the same manner as in Example 1, they were subjected to inoculation tests using the peanut root-knot nematode (*M. arenaria*) and the javanese root-knot nematode (*M. javanica*), and their resistance to these nematodes were evaluated.

As a result, all the tested individuals carrying the SNP markers in resistant-type homozygous form exhibited the root gall severity of 1 or less, so that they were found to be resistant to the root-knot nematodes. In contrast, all the tested individuals carrying the SNP marker in susceptible-type homozygous form exhibited the root gall severity of 3 or more, so that they were found to be susceptible to the root-knot nematodes. These results revealed that the resistance gene located on the resistance gene locus confers resistance not only against the southern root-knot nematode but also against the peanut root-knot nematode and the javanese root-knot nematode.

inoculation test was performed in the same manner as in Example 1. The results thereof are shown in Table 3. In Table 3, "resistant homo" indicates an individual carrying the SNP markers in resistant-type homozygous form; "hetero" indicates an individual carrying the SNP markers in heterozygous form; and "susceptible homo" indicates an individual carrying the SNP markers in susceptible-type homozygous form. As can be seen in Table 3, the individuals indicated as "resistant homo" and "hetero" all exhibited the root gall severity of 1 or less. This demonstrates that the SNP markers are responsible for the root-knot nematode resistance.

TABLE 3

| | Root gall severity | | | | | Total number of individuals | Proportion of individuals with root gall severity of 1 or less |
|---|---|---|---|---|---|---|---|
| | 0 | 1 | 2 | 3 | 4 | | |
| Resistant homo | 11 individuals | 2 individuals | 0 individuals | 0 individuals | 0 individuals | 13 individuals | 100% |
| Hetero | 32 individuals | 2 individuals | 0 individuals | 0 individuals | 0 individual | 34 individuals | 100% |
| Susceptible homo | 0 individuals | 0 individuals | 0 individuals | 4 individuals | 11 individuals | 15 individuals | 0% |

Next, from the 62 lines in the F2 segregating population, three individuals carrying the SNP markers in resistant-type homozygous form and three individuals carrying the SNP markers in susceptible-type homozygous form were selected. They were self-crossed, and seeds were obtained from the thus-obtained 6 lines in the F3 population.

Using the seeds from the 6 lines in the F3 population, 10 individuals were obtained from each line. Then, in the same manner as in Example 1, they were subjected to inoculation tests using the peanut root-knot nematode (*M. arenaria*) and the javanese root-knot nematode (*M. javanica*), and their resistance to these nematodes were evaluated.

As a result, all the tested individuals carrying the SNP markers in resistant-type homozygous form exhibited the root gall severity of 1 or less, so that they were found to be resistant to the root-knot nematodes. In contrast, all the tested individuals carrying the SNP marker in susceptible-type homozygous form exhibited the root gall severity of 3 or more, so that they were found to be susceptible to the root-knot nematodes. These results revealed that the resistance gene located on the resistance gene locus confers resistance not only against the southern root-knot nematode but also against the peanut root-knot nematode and the javanese root-knot nematode.

[Example 5]

An F2 segregating population was prepared, and the correlation between the SNP markers and the root-knot nematode resistance was examined.

An F2 segregating population was newly obtained in the same manner as for the 141 lines in Example 1. Then, with respect to the thus-obtained F2 segregating population, the bases corresponding to the polymorphisms of the SNP markers, solcap_snp_sl_21346 and solcap_snp_sl_21390, were identified in the same manner as in Example 2. Furthermore, from the F2 segregating population, seven individuals carrying the identified SNP markers in genotypes different from each other (plant bodies 1 to 7, also referred to as "seven lines" hereinafter) were selected. Then, with respect to these seven lines, SNP assay was conducted in the same manner as in Example 2 to identify the bases corresponding to the polymorphisms of the SNP markers, solcap_snp_sl_21364, TK43, YU06, YK66, TY38, AR02, HT12, solcap_snp_sl_64250, solcap_snp_sl_21383, and solcap_snp_sl_21385. With respect to these individuals, the root-knot nematode inoculation test was performed in the same manner as in Example 1. The results thereof are shown in Table 4. In Table 4, "A" indicates the presence of the SNP markers in resistant-type homozygous form, "H" indicates the presence of the SNP markers in heterozygous form, and "B" indicates the presence of the SNP markers in susceptible-type homozygous form. In Table 4, A and H are starred. As can be seen in Table 4, the root gall severity was 1 or less in all the individuals carrying YK66, TY38, AR02, and HT12 in resistant-type homozygous form (A) or in heterozygous form (H). From these results, it was found that, among the SNP markers, YK66, TY38, AR02, and HT12 are highly correlated with the root-knot nematode resistance. Also, it was found that, because YK66, TY38, AR02, and HT12 are highly correlated with the root-knot nematode resistance, a region between the sites of YU06 and solcap_snp_sl_64250, which is a region including the above SNP markers, shows high correlation with the root-knot nematode resistance.

TABLE 4

| | solcap_snp_sl_21346 | solcap_snp_sl_21364 | TK43 | YU06 | YK66 | TY38 | AR02 | HT12 | solcap_snp_sl_64250 |
|---|---|---|---|---|---|---|---|---|---|
| Plant body 1 | A* | A* | A* | A* | A* | A* | A* | A* | A* |
| Plant body 2 | H* | H* | H* | H* | H* | H* | H* | H* | H* |
| Plant body 3 | B | B | B | B | B | B | B | B | B |
| Plant body 4 | B | B | B | B | H* | H* | H* | H* | H* |
| Plant body 5 | H* | H* | H* | H* | H* | H* | H* | H* | B |
| Plant body 6 | B | B | B | B | B | B | B | B | H* |
| Plant body 7 | H* | H* | H* | H* | B | B | B | B | B |

| | solcap_snp_sl_21383 | solcap_snp_sl_21385 | solcap_snp_sl_21390 | Root gall severity |
|---|---|---|---|---|
| Plant body 1 | A* | A* | A* | 0 |
| Plant body 2 | H* | H* | H* | 0 |
| Plant body 3 | B | B | B | 3 |
| Plant body 4 | H* | H* | H* | 0 |
| Plant body 5 | B | B | B | 0 |
| Plant body 6 | H* | H* | H* | 3 |
| Plant body 7 | B | B | B | 4 |

While the present invention has been described above with reference to embodiments and examples, the present invention is by no means limited thereto. Various changes and modifications that may become apparent to those skilled in the art may be made in the configuration and specifics of the present invention without departing from the scope of the present invention.

This application claims priority from Japanese Patent Application No. 2013-141865 filed on Jul. 5, 2013. The entire disclosure of this Japanese patent application is incorporated herein by reference.

INDUSTRIAL APPLICABILITY

As specifically described above, the root-knot nematode resistance marker for tomato plants according to the present invention enables easy screening of a root-knot nematode resistant tomato plant, for example. Also, the root-knot nematode resistant tomato plant according to the present invention includes, for example, the root-knot nematode resistance locus on chromosome 4, so that it can exhibit root-knot nematode resistance without depending on temperature conditions in a growing environment, for example- .Also, because the root-knot nematode resistant tomato plant according to the present invention includes, for example, a dominant resistance gene locus, it is possible to obtain progenies exhibiting root-knot nematode resistance inherited dominantly by crossing with other tomato plants. Furthermore, because the present invention can eliminate the necessity of soil treatments performed conventionally, the problem of labor and cost by the soil treatments also can be avoided, for example.

The invention claimed is:

1. A method of producing a root-knot nematode resistant tomato plant, the method comprising:

detecting, in one or more tomato plants to be examined, marker TY38 corresponding to the 21st nucleotide of SEQ ID NO: 22 to identify a root-knot nematode resistance locus on chromosome 4 and select a root-knot nematode resistant tomato plant comprising the marker, and crossing the root-knot nematode resistant tomato plant comprising the root-knot nematode resistance locus on chromosome 4 with a cultivated tomato plant to produce a progeny plant, wherein the progeny plant has the root-knot nematode resistance locus on chromosome 4.

2. The method according to claim 1, wherein
   the detecting comprises detecting at least one polynucleotide selected from the group consisting of
   (a) a polynucleotide consisting of the sequence of SEQ ID NO: 22, and
   (b) a polynucleotide consisting of a sequence having at least 90% identity to the sequence of the polynucleotide (a) with the 21st nucleotide (A) in the sequence of the polynucleotide (a) being conserved and having a function equivalent to that of the polynucleotide (a) the root-knot nematode resistance in the root-knot nematode resistance locus.

3. The method according to claim 1, wherein the detecting comprises detecting a sequence in a region between sites of two SNP markers of YU06 corresponding to the 55th nucleotide of SEQ ID NO: 19 and solcap_snp_sl_64250 corresponding to the 16th nucleotide of SEQ ID NO: 13 on the chromosome 4.

4. The method according to claim 3, wherein
   the root-knot nematode resistance locus comprises the SNP markers of YK66 corresponding to the 16th nucleotide of SEQ ID NO: 21, TY38 corresponding to the 21st nucleotide of SEQ ID NO: 22, AR02 corresponding to the 16th nucleotide of SEQ ID NO: 23, and HT12 corresponding to the 26th nucleotide of SEQ ID NO: 24 in a region between sites of YU06 corresponding to the 55th nucleotide of SEQ ID NO: 19 and solcap_snp_sl_64250 corresponding to the 16th nucleotide of SEQ ID NO: 13 on the chromosome 4.

5. The method according to claim 4, wherein
   the root-knot nematode resistance locus comprises the SNP markers of TK43 corresponding to the 16th and 17th nucleotides of SEQ ID NO: 18 and YU06 corresponding to the 55th nucleotide of SEQ ID NO: 19 in a region between sites of solcap_snp_sl_21364 corresponding to the 16th nucleotide of SEQ ID NO: 17 and YK66 corresponding to the 16th nucleotide of SEQ ID NO: 21 on the chromosome 4, the root-knot nematode resistance locus comprises the SNP markers of solcap_snp_sl_64250 corresponding to the 16th nucleotide of SEQ ID NO: 13 and solcap_snp_sl_21383 corresponding to the 16th nucleotide of SEQ ID NO: 14 in a region between sites of HT12 corresponding to the 26th nucleotide of SEQ ID NO: 24 and solcap_snp_sl_21385 corresponding to the 37th nucleotide of SEQ ID NO: 16 on the chromosome 4, the root-knot nematode resistance locus comprises the SNP markers of solcap_snp_sl_21346 corresponding to the 21st nucleotide of SEQ ID NO: 15 and solcap_snp_sl_21364 corresponding to the 16th nucleotide of SEQ ID NO: 17 in a region between sites of solcap_snp_sl_21346 and TK43 corresponding to the 16th and 17th nucleotides of SEQ ID NO: 18 on the chromosome 4, and the root-knot nematode resistance locus comprises the SNP markers of solcap_snp_sl_21385 corresponding to the 37th nucleotide of SEQ ID NO: 16 and solcap_snp_sl_21390 corresponding to the 16th nucleotide of SEQ ID NO: 20 in a region between sites of solcap_snp_sl_21383 corresponding to the 16th nucleotide of SEQ ID NO: 14 and solcap_snp_sl_21390 on the chromosome 4.

6. A method of producing a root-knot nematode resistant tomato plant, the method comprising
   crossing a root-knot nematode resistant tomato plant comprising a root-knot nematode resistance locus on chromosome 4 with a cultivated tomato plant to produce a progeny plant, wherein the progeny plant has the root-knot nematode resistance locus on chromosome 4, and
   detecting, in the progeny plant or progeny lines thereof, marker TY38 corresponding to the 21st nucleotide of SEQ ID NO: 22
   to identify a root-knot nematode resistance locus comprising the marker on chromosome 4.

7. The method according to claim 6, wherein
   the detecting comprises detecting at least one polynucleotide selected from the group consisting of
   (a) a polynucleotide consisting of the sequence of SEQ ID NO: 22, and
   (b) a polynucleotide consisting of a sequence having at least 90% identity to the sequence of the polynucleotide (a) with the 21st nucleotide (A) in the sequence of the polynucleotide (a) being conserved and having a function equivalent to that of the polynucleotide (a) regarding the root-knot nematode resistance in the root-knot nematode resistance locus.

8. The method according to claim 6, wherein the detecting comprises detecting a sequence in a region between sites of two SNP markers of YU06 corresponding to the 55th nucleotide of SEQ ID NO: 19 and solcap_snp_sl_64250 corresponding to the 16th nucleotide of SEQ ID NO: 13 on the chromosome 4.

9. The method according to claim 8, wherein
the root-knot nematode resistance locus comprises the SNP markers of YK66 corresponding to the 16th nucleotide of SEQ ID NO: 21, TY38 corresponding to the 21st nucleotide of SEQ ID NO: 22, AR02 corresponding to the 16th nucleotide of SEQ ID NO: 23, and HT12 corresponding to the 26th nucleotide of SEQ ID NO: 24 in a region between sites of YU06 corresponding to the 55th nucleotide of SEQ ID NO: 19 and solcap_snp_sl_64250 corresponding to the 16th nucleotide of SEQ ID NO: 13 on the chromosome 4.

10. The method according to claim 9, wherein
the root-knot nematode resistance locus comprises the SNP markers of TK43 corresponding to the 16th and 17th nucleotides of SEQ ID NO: 18 and YU06 corresponding to the 55th nucleotide of SEQ ID NO: 19 in a region between sites of solcap_snp_sl_21364 corresponding to the 16th nucleotide of SEQ ID NO: 17 and YK66 corresponding to the 16th nucleotide of SEQ ID NO: 21 on the chromosome 4,
the root-knot nematode resistance locus comprises the SNP markers of solcap_snp_sl_64250 corresponding to the 16th nucleotide of SEQ ID NO: 13 and solcap_snp_sl_21383 corresponding to the 16th nucleotide of SEQ ID NO: 14 in a region between sites of HT12 corresponding to the 26th nucleotide of SEQ ID NO: 24 and solcap_snp_sl_21385 corresponding to the 37th nucleotide of SEQ ID NO: 16 on the chromosome 4,
the root-knot nematode resistance locus comprises the SNP markers of solcap_snp_sl_21346 corresponding to the 21st nucleotide of SEQ ID NO: 15 and solcap_snp_sl_21364 corresponding to the 16th nucleotide of SEQ ID NO: 17 in a region between sites of solcap_snp_sl_21346 corresponding to the 21st nucleotide of SEQ ID NO: 15 and TK43 corresponding to the 16th and 17th nucleotides of SEQ ID NO: 18 on the chromosome 4, and
the root-knot nematode resistance locus comprises the SNP markers of solcap_snp_sl_21385 corresponding to the 37th nucleotide of SEQ ID NO: 16 and solcap_snp_sl_21390 corresponding to the 16th nucleotide of SEQ ID NO: 20 in a region between sites of solcap_snp_sl_21383 corresponding to the 16th nucleotide of SEQ ID NO: 14 and solcap_snp_sl_21390 corresponding to the 16th nucleotide of SEQ ID NO: 20 on the chromosome 4.

11. The method according to claim 1, wherein
the root-knot nematode resistant tomato plant is a tomato plant deposited with the International Patent Organism Depositary of the National Institute of Technology and Evaluation under Accession No. FERM BP-22251 or a progeny line thereof,
wherein the progeny line comprises the root-knot nematode resistance locus on chromosome 4.

12. The method according to claim 1, further comprising detecting a root-knot nematode resistant tomato plant from one or more tomato plants obtained from the crossing or progeny lines thereof.

13. The method according to claim 6, wherein
the root-knot nematode resistant tomato plant is a tomato plant deposited with the International Patent Organism Depositary of the National Institute of Technology and Evaluation under Accession No. FERM BP-22251 or a progeny line thereof,
wherein the progeny line comprises the root-knot nematode resistance locus on chromosome 4.

14. The method according to claim 1, wherein the cultivated tomato plant is S. lycopersicum.

15. The method according to claim 6, wherein the cultivated tomato plant is S. lycopersicum.

16. The method according to claim 1, further comprising detecting, in the one or more tomato plants to be examined, YK66 corresponding to the 16th nucleotide of SEQ ID NO: 21 on the chromosome 4.

17. The method according to claim 1, further comprising detecting, in the one or more tomato plants to be examined, AR02 corresponding to the 16th nucleotide of SEQ ID NO: 23 on the chromosome 4.

18. The method according to claim 1, further comprising detecting, in the one or more tomato plants to be examined, HT12 corresponding to the 26th nucleotide of SEQ ID NO: 24 on the chromosome 4.

19. The method according to claim 6, further comprising detecting, in the progeny plant or progeny lines thereof, YK66 corresponding to the 16th nucleotide of SEQ ID NO: 21 on the chromosome 4.

20. The method according to claim 6, further comprising detecting, in the progeny plant or progeny lines thereof, AR02 corresponding to the 16th nucleotide of SEQ ID NO: 23 on the chromosome 4.

21. The method according to claim 6, further comprising detecting, in the progeny plant or progeny lines thereof, HT12 corresponding to the 26th nucleotide of SEQ ID NO: 24 on the chromosome 4.

* * * * *

SEQUENCE LISTING

```
<160> NUMBER OF SEQ ID NOS: 34

<210> SEQ ID NO 1
<211> LENGTH: 101
<212> TYPE: DNA
<213> ORGANISM: Solanum Lycopersicum

<400> SEQUENCE: 1
atgctttctt caactccgac ttctgtaata ccagaattta tcgtggtgga ggttccggga      60
actgcatgga ggaaggtttt aaccccagtt caatccatat a                         101

<210> SEQ ID NO 2
<211> LENGTH: 116
<212> TYPE: DNA
<213> ORGANISM: Solanum Lycopersicum

<400> SEQUENCE: 2
cgtacagctg catagctttc tcaatctcct tattcctaga caactcttct attagaacgc      60
cataaacaga aatgtccagc acaaaaccca atttcttcat tttatccaac agttgc         116

<210> SEQ ID NO 3
<211> LENGTH: 101
<212> TYPE: DNA
<213> ORGANISM: Solanum Lycopersicum

<400> SEQUENCE: 3
ttggagatcg ggtcagcttg tgtgccacag aggagagggt ttgaagacga ggcaagaatc      60
tggcatctta tgcaacaaaa acctttagat caagggaaat t                         101

<210> SEQ ID NO 4
<211> LENGTH: 101
<212> TYPE: DNA
<213> ORGANISM: Solanum Lycopersicum

<400> SEQUENCE: 4
cgaaatgctc ttttttcctt tacaccatgt gactgattat agtcttactt taatgaataa      60
gcaactgaat acaaaaatta tcacctctat atagatacag t                         101

<210> SEQ ID NO 5
<211> LENGTH: 101
<212> TYPE: DNA
<213> ORGANISM: Solanum Lycopersicum

<400> SEQUENCE: 5
tctccggcga ccggagaatc ctacgcctgt aaatctatcg ataaaaacct tctcattgat      60
tccaccgacc gtgagtgtct cgataaagaa cccaaaattc t                         101
```

<210> SEQ ID NO 6
<211> LENGTH: 101
<212> TYPE: DNA
<213> ORGANISM: Solanum Lycopersicum

<400> SEQUENCE: 6
agtggcttta tgctctacta gggagcacgg gcgctgcaat atttggttcc tttaatcccc    60
tcttggccta tgtcattgca ttgattgtaa cagcatatta c                       101

<210> SEQ ID NO 7
<211> LENGTH: 99
<212> TYPE: DNA
<213> ORGANISM: Solanum Lycopersicum

<400> SEQUENCE: 7
ttgccagcag agcggtccac gttggcgagg cggtactcgt gcataatcca attggttttt    60
atacctctgg gtgcttttcc ggcatagaac acaagtgcc                          99

<210> SEQ ID NO 8
<211> LENGTH: 101
<212> TYPE: DNA
<213> ORGANISM: Solanum Lycopersicum

<400> SEQUENCE: 8
tggtgaagaa gcttgatcga gttggtgccc gccttgttag tagcaattca tgatgatcga    60
tggatcaatc aatcaatcaa ctatgcctca attccaaacg a                       101

<210> SEQ ID NO 9
<211> LENGTH: 132
<212> TYPE: DNA
<213> ORGANISM: Solanum Lycopersicum

<400> SEQUENCE: 9
taacaaaagg caaattaatg ggaacaaggg actgacatca ggagcttcca aagtcatatt    60
ttaggtctta ggcaaagaag gtgataattt aactgtatga tccccatcag gccttcaaag   120
acattgctaa aa                                                       132

<210> SEQ ID NO 10
<211> LENGTH: 105
<212> TYPE: DNA
<213> ORGANISM: Solanum Lycopersicum

<400> SEQUENCE: 10
agctaaagat atggtggaaa agtgtagagg cttacctctt gcaatcgttg tattgagcgg    60
actactttca cataaaaggg ggctagacca atggcaaaaa gtgaa                   105

<210> SEQ ID NO 11
<211> LENGTH: 106
<212> TYPE: DNA
<213> ORGANISM: Solanum Lycopersicum

<400> SEQUENCE: 11
gctgtgcaat gacttttgca ttcaggtcct ggaacttggg gcattgacag tgctgatgaa    60
gatgatgaaa tctcacacca cggaagaagc tgtaaaagca ttattt                  106

<210> SEQ ID NO 12
<211> LENGTH: 116
<212> TYPE: DNA

<213> ORGANISM: Solanum Lycopersicum

<400> SEQUENCE: 12
tattcatgaa caaaaaacag tgagaaaaat gtgtcatacg actcaaactc attcagccaa    60
agacgtctat caatattgtc cagttattaa taataactttt ttttttttct gtttgc       116

<210> SEQ ID NO 13
<211> LENGTH: 31
<212> TYPE: DNA
<213> ORGANISM: Solanum Lycopersicum

<400> SEQUENCE: 13
agggtttgaa gacgaggcaa gaatctggca t    31

<210> SEQ ID NO 14
<211> LENGTH: 31
<212> TYPE: DNA
<213> ORGANISM: Solanum Lycopersicum

<400> SEQUENCE: 14
attatagtct tactttaatg aataagcaac t    31

<210> SEQ ID NO 15
<211> LENGTH: 41
<212> TYPE: DNA
<213> ORGANISM: Solanum Lycopersicum

<400> SEQUENCE: 15
ccagaattta tcgtggtgga ggttcttgga actgcatgga g    41

<210> SEQ ID NO 16
<211> LENGTH: 79
<212> TYPE: DNA
<213> ORGANISM: Solanum Lycopersicum

<400> SEQUENCE: 16
agaatcctac gcctgtaaat ctatcgacaa aaaccttctc attgattcca ccgaccgtga    60
gtgtctcgat aaagaaccc    79

<210> SEQ ID NO 17
<211> LENGTH: 31
<212> TYPE: DNA
<213> ORGANISM: Solanum Lycopersicum

<400> SEQUENCE: 17
gttagtagca attcatgatg atcgatggat c    31

<210> SEQ ID NO 18
<211> LENGTH: 32
<212> TYPE: DNA
<213> ORGANISM: Solanum Lycopersicum

<400> SEQUENCE: 18
aagaaggtga atatttaact gtatgatccc ca    32

<210> SEQ ID NO 19
<211> LENGTH: 122
<212> TYPE: DNA
<213> ORGANISM: Solanum Lycopersicum

<400> SEQUENCE: 19
ggtaaggata gctaaagata tggtggaaaa gtgtagaggc ttacctcttg caatcgttgt    60

```
attgagcgga ctactttcac ataaaagggg gctagaccaa tggcaaaaag tgaaagatca      120
ct                                                                    122

<210> SEQ ID NO 20
<211> LENGTH: 31
<212> TYPE: DNA
<213> ORGANISM: Solanum Lycopersicum

<400> SEQUENCE: 20
gcaatatttg gttcctttaa tcccctcttg g                                     31

<210> SEQ ID NO 21
<211> LENGTH: 31
<212> TYPE: DNA
<213> ORGANISM: Solanum Lycopersicum

<400> SEQUENCE: 21
ctcaaactca ttcagccaaa gacgtctatc a                                     31

<210> SEQ ID NO 22
<211> LENGTH: 41
<212> TYPE: DNA
<213> ORGANISM: Solanum Lycopersicum

<400> SEQUENCE: 22
ctagacaact cttctattag aacaccataa acagaaatgt c                          41

<210> SEQ ID NO 23
<211> LENGTH: 31
<212> TYPE: DNA
<213> ORGANISM: Solanum Lycopersicum

<400> SEQUENCE: 23
ggcattgaca gtgctgatga agatgatgaa a                                     31

<210> SEQ ID NO 24
<211> LENGTH: 51
<212> TYPE: DNA
<213> ORGANISM: Solanum Lycopersicum

<400> SEQUENCE: 24
gaaaagcacc tagaggaata aaaccaatt ggattatgca cgagtaccgc c                51

<210> SEQ ID NO 25
<211> LENGTH: 84
<212> TYPE: DNA
<213> ORGANISM: Solanum Lycopersicum

<400> SEQUENCE: 25
aatctcctta ttcctagaca actcttctat tagaacacca taaacagaaa tgtccagcac      60
aaaacccaat ttcttcattt tatc                                             84

<210> SEQ ID NO 26
<211> LENGTH: 141
<212> TYPE: DNA
<213> ORGANISM: Solanum Lycopersicum

<400> SEQUENCE: 26
gctattgtat tgacgctgtg caatgacttt tgcattcagg tcctggaact tggggcattg      60
acagtgctga tgaagatgat gaaatctcac accacagaag aagctgtaaa agcattattt     120
```
gctatttcag cactaataag a                                            141

<210> SEQ ID NO 27
<211> LENGTH: 75
<212> TYPE: DNA
<213> ORGANISM: Solanum Lycopersicum

<400> SEQUENCE: 27
agaaggcact tgtgttctat gccggaaaag cacctagagg aataaaaacc aattggatta   60
tgcacgagta ccgcc                                                   75

<210> SEQ ID NO 28
<211> LENGTH: 61
<212> TYPE: DNA
<213> ORGANISM: Solanum Lycopersicum

<400> SEQUENCE: 28
acagaggaga gggtttgaag acgaggcaag aatctggcat cttatgcaac aaaaaccttt   60
a                                                                  61

<210> SEQ ID NO 29
<211> LENGTH: 88
<212> TYPE: DNA
<213> ORGANISM: Solanum Lycopersicum

<400> SEQUENCE: 29
tcttcaactc cgacttctgt aataccagaa tttatcgtgg tggaggttct tggaactgca   60
tggaggaagg ttttaacccc agttcaat                                     88

<210> SEQ ID NO 30
<211> LENGTH: 60
<212> TYPE: DNA
<213> ORGANISM: Solanum Lycopersicum

<400> SEQUENCE: 30
gcgctgcaat atttggttcc tttaatcccc tcttggccta tgtcattgca ttgattgtaa   60

<210> SEQ ID NO 31
<211> LENGTH: 82
<212> TYPE: DNA
<213> ORGANISM: Solanum Lycopersicum

<400> SEQUENCE: 31
tgaagaagct tgatcgagtt ggtgcccgcc ttgttagtag caattcatga tgatcgatgg   60
atcaatcaat caatcaacta tg                                           82

<210> SEQ ID NO 32
<211> LENGTH: 92
<212> TYPE: DNA
<213> ORGANISM: Solanum Lycopersicum

<400> SEQUENCE: 32
aatgggaaca agggactgac atcaggagct tccaaagaag gtgaatattt aactgtatga   60
tccccatcag gccttcaaag acattgctaa aa                                92

<210> SEQ ID NO 33
<211> LENGTH: 61
<212> TYPE: DNA
<213> ORGANISM: Solanum Lycopersicum

<400> SEQUENCE: 33

```
cctttacacc atgtgactga ttatagtctt actttaatga ataagcaact gaatacaaaa        60
a                                                                        61

<210> SEQ ID NO 34
<211> LENGTH: 105
<212> TYPE: DNA
<213> ORGANISM: Solanum Lycopersicum

<400> SEQUENCE: 34
ttttattcat gaacaaaaaa cagtgagaaa aatgtgtcat acgactcaaa ctcattcagc        60
caaagacgtc tatcaatatt gtccagttat taataataac ttttt                      105
```